(12) United States Patent
Kitagawa

(10) Patent No.: US 12,221,597 B2
(45) Date of Patent: Feb. 11, 2025

(54) METHOD OF CULTURING CELL, METHOD OF MANUFACTURING CELL SUPPORT COMPLEX, CULTURED CELL, AND CELL SUPPORT COMPLEX

(71) Applicant: NIKKISO CO., LTD., Tokyo (JP)

(72) Inventor: Fumihiko Kitagawa, Kanazawa (JP)

(73) Assignee: NIKKISO CO., LTD., Tokyo (JP)

( * ) Notice: Subject to any disclaimer, the term of this patent is extended or adjusted under 35 U.S.C. 154(b) by 1104 days.

(21) Appl. No.: 17/006,138

(22) Filed: Aug. 28, 2020

(65) Prior Publication Data

US 2020/0392442 A1 Dec. 17, 2020

Related U.S. Application Data

(63) Continuation of application No. PCT/JP2019/011389, filed on Mar. 19, 2019.

(30) Foreign Application Priority Data

Mar. 22, 2018 (JP) .................. 2018-054310

(51) Int. Cl.
C12M 1/00 (2006.01)
C12M 1/06 (2006.01)

(52) U.S. Cl.
CPC ............ C12M 23/20 (2013.01); C12M 27/02 (2013.01)

(58) Field of Classification Search
None
See application file for complete search history.

(56) References Cited

U.S. PATENT DOCUMENTS

| 2008/0166328 A1 | 7/2008 | Harmon et al. |
| 2008/0267921 A1 | 10/2008 | Marban et al. |
| 2011/0318725 A1 | 12/2011 | Suenaga et al. |
| 2016/0281062 A1 | 9/2016 | Zink et al. |

FOREIGN PATENT DOCUMENTS

| EP | 3608398 A1 | 2/2020 |
| JP | 2003219865 A | 8/2003 |
| JP | 2011030453 A | 2/2011 |
| JP | 2011050358 A | 3/2011 |
| JP | 2014515270 A | 6/2014 |
| JP | 2015511487 A | 4/2015 |
| WO | WO-2010103748 A1 | 9/2010 |
| WO | WO 2011/141914 A1 | 11/2011 |
| WO | WO-2013187359 A1 | 12/2013 |
| WO | WO-2015167003 A1 | 11/2015 |
| WO | WO-2016019168 A1 | 2/2016 |
| WO | WO-2016063935 A1 | 4/2016 |
| WO | WO-2017082024 A1 | 5/2017 |
| WO | WO-2017082025 A1 | 5/2017 |
| WO | WO-2017082026 A1 | 5/2017 |
| WO | WO-2017126647 A1 | 7/2017 |
| WO | WO-2008047760 A1 | 4/2018 |
| WO | WO-2018186185 A1 | 10/2018 |

OTHER PUBLICATIONS

Fok et al. Shear-Controlled Single-Step Mouse Embryonic Stem Cell Expansion and Embryoid Body-Based Differentiation (2005), Stem Cells, 23, pp. 1333-1342. (Year: 2005).*
An Office Action in corresponding U.S. Appl. No. 16/593,462 dated Jul. 13, 2023 is attached, 25 pages.
Office Action mailed Mar. 3, 2022 in EP Application No. 18 780 473.7, 8 pages.
International Search Report issued in corresponding PCT Application No. PCT/JP2018/011392 dated Jun. 19, 2018. (total pp. 8).
Written Opinion issued by the International Searching Authority in corresponding PCT Application No. PCT/JP2018/011392 dated Jun. 19, 2018. (total pp. 12).
Written Opinion issued by the International Preliminary Examining Authority in corresponding PCT Application No. PCT/JP2018/011392 dated May 7, 2019. (total pages ).
International Preliminary on Patentability issued in corresponding PCT Application No. PCT/JP2018/011392 dated Jul. 29, 2019. (total pp. 21).
International Search Report issued in corresponding PCT Application No. PCT/JP2019/011389 dated Jun. 6, 2018. (total pp. 5).
Written Opinion issued by the International Searching Authority in corresponding PCT Application No. PCT/JP2018/011389 dated Jun. 18, 2019. (total pp. 21).
Written Opinion issued by the International Preliminary Examining Authority in corresponding PCT Application No. PCT/JP2018/011389 dated Mar. 31, 2020. (total pp. 18).
International Preliminary on Patentability issued in corresponding PCT Application No. PCT/JP2018/011389 dated Jun. 16, 2020. (total pp. 21).
Buzhor, E., et al., "Kidney Spheroids Recapitulate Tubular Organoids Leading to Enhanced Tubulogenic Potency of Human Kidney-Derived Cells", Tissue Engineering: Part A, 2011, vol. 17, No. 17-18, pp. 2305-2319, in particular, abstract, p. 2306, left column, lines 24-51, p. 2309, left column, line 1 to p. 2312, left column, line 5, (total pp. 15).
Gao X., et al.; "Basic structure and cell culture condition of a bioartificial renal tubule on chip towards a cell-based separation microdevice"; Analytical Sciences, 2011, vol. 27, pp. 907-912, abstract, p. 909, "Results and discussion", second paragraph. (total pp. 6).
Lewis M. P., et al.; "Pexicrine effects of basement membrane components on paracrine signaling by renal tubular cells"; Kidney International, 1996, vol. 49, pp. 48-58, abstract, fig. 1. (total pp. 11).
Kusamori, Kosuke, et al.; "Development of multicellular spheroid for cell-based therapy"; Drug Delivery System, 2013, vol. 28, No. 1, pp. 45-53. (total pp. 9).

(Continued)

Primary Examiner — Kara D Johnson
Assistant Examiner — Maytee Marie Contes De Jesus
(74) Attorney, Agent, or Firm — MUNCY, GEISSLER, OLDS & LOWE, P.C.

(57) ABSTRACT

A method of culturing cells includes culturing the cell in a cell suspension under repetitive cycles of stirring and rest while keeping the cell non-adherent to a culture vessel, so as to form at least one aggregate of the cells.

11 Claims, 15 Drawing Sheets

(56) References Cited

OTHER PUBLICATIONS

Office Action and Search Report of the corresponding Japanese Patent Application No. 2019-511143 issued on Sep. 23, 2020. (total pp. 8).
Prange et al., "Human proximal tubule vells form functional microtissues," Pflugers Arch—Eur J Physiol (2016) vol. 468, pp. 739-750.
Office Action mailed Apr. 27, 2021 in JP Application No. 2019-511143, 8 pages.
Office Action mailed Jun. 29, 2021 in JP Application No. 2019-507828, 8 pages.
Hall et al., "Lumen formation by epithelial cell lines in response to collagen overlay: A morphogenetic model in culture," Proc. Natl. Acad. Sci., USA, vol. 79, pp. 4672-4676, Aug. 1982, Cell Biology.
Hoppensack et al., "A Human In Vitro Model That Mimics the Renal Proximal Tubule," Tissue Engineering: Part C, vol. 20, No. 7, 2014, 11 pages.
Tufro, Alda, "Podocyte Shape Regulation by Semaphorin 3A and MICAL-1," Semaphorin Signaling: Methods and Protocols, Methods in Molecular Biology, vol. 1493, 7 pages.
Office Action issued Jun. 7, 2022 in U.S. Appl. No. 16/593,462, 17 pages.
Forbes, Michael S. et al., Proximal tubular injury and rapid formation of atubular glomeruli in mice with unilateral ureteral obstruction: a new look at an old model, Mar. 23, 2011, 8 pages, Am J Physiol Renal Physiol.
Office Action of corresponding U.S. Appl. No. 16/593,462 dated Dec. 13, 2022, 22 pages.
Office Action of U.S. Appl. No. 16/593,462, dated Dec. 8, 2021, 15 pages.
Office Action of European Patent Application No. 19770657.5, dated Dec. 22, 2021, 10 pages.
Andersen et al., "Biochemical and Ultrastructural Characterization of Fluid Transporting LLC-PK1 Microspheres," J Am Soc Nephrol 9: 1153-1168, 16 pages.
Wohlfarth et al., "Protein uptake disturbs collagen homeostasis in proximal tubule-derived cells," Kidney International, vol. 63, Supplement 84 (2003), pp. S103-S109, 7 pages.
Extended European Search Report issued for related EP Patent Application No. 18780473.7 dated Nov. 11, 2020.
Office Action dated Oct. 4, 2023 issued in corresponding European Application No. 18780473.7 (full English text), 6 pages.

* cited by examiner

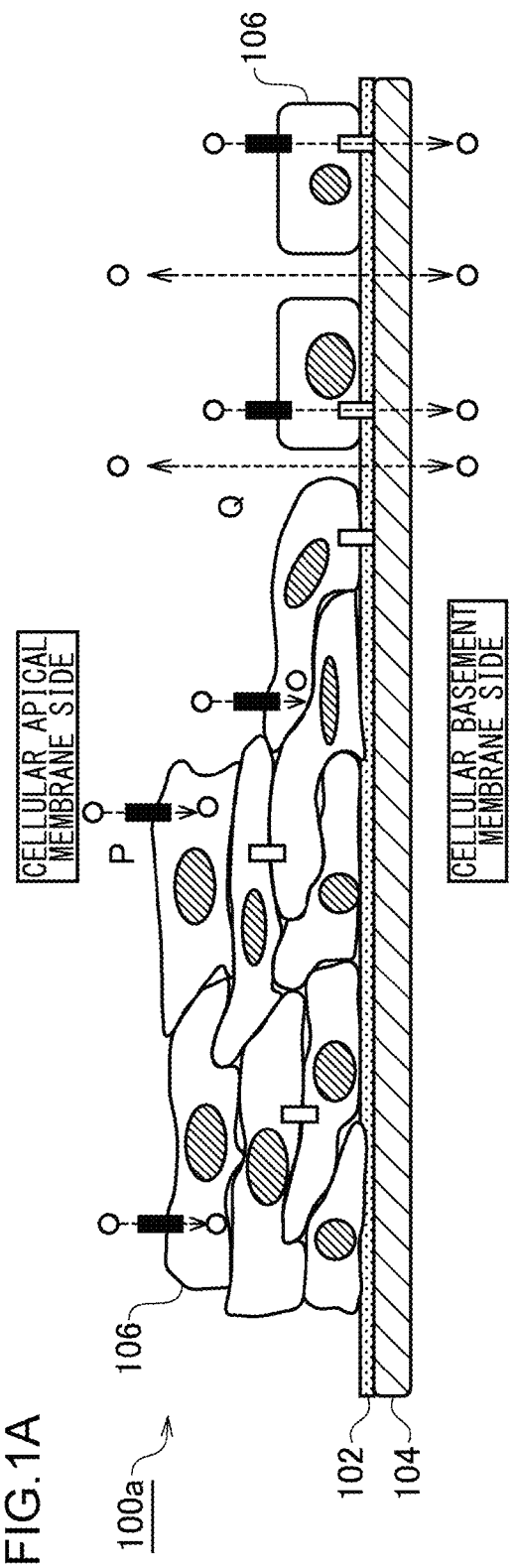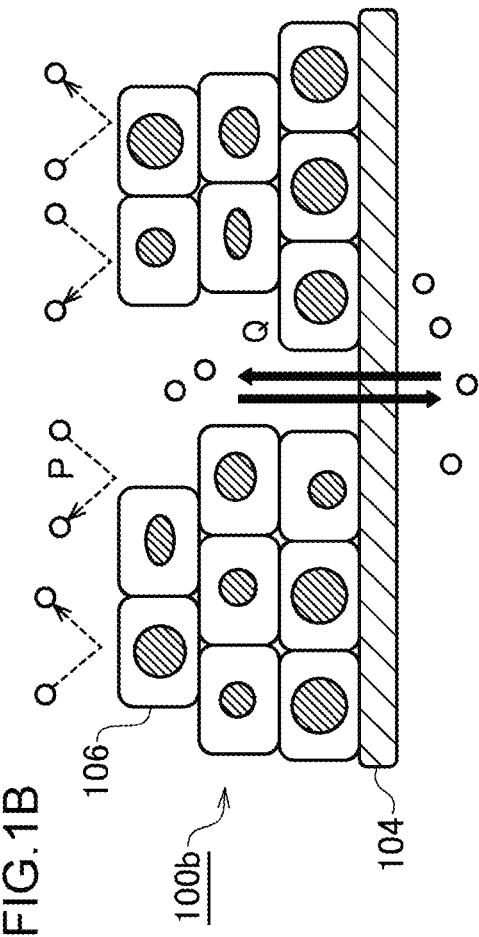

FIG.6

| gene | Acronym | day4/day0 |
|---|---|---|
| aquaporin 1 | *AQP1* | 0.412 |
| alanyl aminopeptidase | *CD13* | 0.039 |
| sodium glucose cotransporter 2 | *SGLT2* | 0.003 |
| $Na^+/K^+$ ATPase | *Na/K ATPase* | 0.138 |
| peptide transporter 1 | *PEPT1* | 0.465 |
| multiple drug resistance 1 | *MDR1* | 0.325 |
| organic anion transporter 1 | *OAT1* | 0.208 |
| organic cation transporter novel 1 | *OCTN2* | 0.031 |
| E-cadherin | *E-cadherin* | 0.005 |
| zonula occludens-1 | *ZO-1* | 0.176 |

FIG.7

| GENE | | NUMBER OF SEEDED CELLS | NUMBER OF DAYS OF CULTURE (DAY) | |
|---|---|---|---|---|
| | | | 3 | 7 |
| | AQP1 | 500 | 11.5 | 7.4 |
| | | 1000 | 10.7 | 8.3 |
| | | 2500 | 8.9 | 8.8 |
| | | 5000 | 0.6 | 5.6 |
| | | 10000 | 0.8 | 1.7 |
| | | 25000 | 0.1 | 0.4 |
| | | COMPARATIVE EXAMPLE | 0.01 | 0.2 |
| | SGLT2 | 500 | 33.4 | 68.3 |
| | | 1000 | 32.7 | 73.2 |
| | | 2500 | 25.9 | 66.7 |
| | | 5000 | 26.3 | 60.2 |
| | | 10000 | 23.9 | 59.0 |
| | | 25000 | 18.7 | 59.8 |
| | | COMPARATIVE EXAMPLE | 1.6 | 18.2 |
| | OAT1 | 500 | 1.1 | 503000.0 |
| | | 1000 | 1.0 | 761000.0 |
| | | 2500 | 1.8 | 100000.0 |
| | | 5000 | 1.9 | 112000.0 |
| | | 10000 | 2.3 | 31800.0 |
| | | 25000 | 1.5 | 279.0 |
| | | COMPARATIVE EXAMPLE | 16.4 | 473.2 |

FIG.8

| GENE | NUMBER OF SEEDED CELLS | NUMBER OF DAYS OF CULTURE (DAY) | | | | | | | | |
|---|---|---|---|---|---|---|---|---|---|---|
| | | 3 | 4 | 5 | 6 | 7 | 8 | 10 | 12 | 14 |
| AQP1 | 1000 | 5.9 | 4.6 | 10.2 | 14.8 | 19.2 | 31.6 | 35.7 | 7.3 | 13.3 |
| SGLT2 | | 65.0 | 99.5 | 116.5 | 131.9 | 230.0 | 225.1 | 382.8 | 484.9 | 641.1 |
| OAT1 | | 2.2 | 1.2 | 98355.0 | 368105.3 | 1260000.0 | 1065602.1 | 1743202.4 | 921018.6 | 252611.1 |

|  | STIRRING SPEED/NUMBER OF DAYS OF CULTURE | | | | | | | | |
|---|---|---|---|---|---|---|---|---|---|
|  | 30rpm | | 40rpm | | 60rpm | | 75rpm | | control |
|  | 3days | 7days | 3days | 7days | 3days | 7days | 3days | 7days | 7days |
| AGGREGATE FORMATION | × | × | × | × | × | × | × | × | ○ |

STIRRING INTERRUPTION TIME  0min           Control
STIRRING SPEED              60rpm

| | STIRRING SPEED/NUMBER OF DAYS OF CULTURE | | | | | | | | |
|---|---|---|---|---|---|---|---|---|---|
| | 30rpm | | 40rpm | | 60rpm | | 75rpm | | control |
| GENE | 3days | 7days | 3days | 7days | 3days | 7days | 3days | 7days | 7days |
| AQP1 | 5.17E-03 | 4.26E-03 | 1.15E-03 | 5.63E-03 | 2.03E-03 | 6.24E-04 | 5.17E-03 | 4.26E-03 | 1 |
| OAT1 | 4.63E-04 | 5.14E-05 | 5.14E-05 | 4.63E-04 | 1.84E-02 | 4.17E-02 | 5.14E-05 | 1.60E-02 | 1 |

FIG.10

|  | STIRRING SPEED/NUMBER OF DAYS OF CULTURE | | | | |
|---|---|---|---|---|---|
|  | 30rpm | 40rpm | 60rpm | 75rpm | control |
| GENE | 7days | 7days | 7days | 7days | 7days |
| AQP1 | 1.98 | 2.12 | 1.74 | 1.06 | 1 |
| OAT1 | 1.08 | 0.93 | 0.78 | 0.57 | 1 |

FIG.12

| | STIRRING SPEED/NUMBER OF DAYS OF CULTURE | | | | |
|---|---|---|---|---|---|
| | 20rpm | 30rpm | 40rpm | 60rpm | 75rpm |
| 0min | △ | × | × | × | × |
| 5min | △ | △ | △ | △ | △ |
| 10min | △ | ○ | ○ | ○ | ○ |
| 30min | △ | ○ | ○ | ○ | ○ |
| 60min | △ | △ | ○ | ○ | ○ |
| 120min | △ | △ | ○ | ○ | ○ |
| 240min | △ | △ | ○ | ○ | ○ |
| 480min | △ | △ | △ | △ | △ |

REST TIME

FIG.13

| | STIRRING SPEED/STIRRING INTERRUPTION TIME | | | | | control |
|---|---|---|---|---|---|---|
| | 40rpm | | | | | |
| GENE | 0min | 5min | 10min | 60min | 240min | |
| AQP1 | 5.63E-03 | 2.63E-02 | 0.89 | 0.91 | 0.84 | 1 |
| OAT1 | 4.63E-04 | 8.63E-02 | 0.91 | 0.88 | 0.72 | 1 |

FIG.14

| | STIRRING SPEED/STIRRING INTERRUPTION TIME | | | | control |
|---|---|---|---|---|---|
| | 30rpm | 40rpm | 60rpm | 75rpm | |
| GENE | 10min | | | | |
| AQP1 | 0.74 | 1.03 | 1.46 | 1.04 | 1 |
| OAT1 | 1.04 | 0.96 | 0.83 | 0.62 | 1 |

METHOD OF CULTURING CELL, METHOD OF MANUFACTURING CELL SUPPORT COMPLEX, CULTURED CELL, AND CELL SUPPORT COMPLEX

CROSS-REFERENCE TO RELATED APPLICATIONS

This application is based upon and claims the benefit of priority from the prior Japanese Patent Application No. 2018-054310, filed on Mar. 22, 2018, and International Patent Application No. PCT/JP2019/011389, filed on Mar. 19, 2019, the entire content of each of which is incorporated herein by reference.

BACKGROUND

Field of the Invention

The present invention relates to a method of culturing cells, a method of manufacturing a cell support complex, a cultured cell, and a cell support complex.

Description of the Related Art

In recent years, development has proceeded to create a module as a bioartificial kidney which can substitute renal function of patients with renal failure, having a polymer membrane such as a hollow fiber membrane, hybridized with a renal cell (cell having renal function) such as proximal tubule epithelial cell. In particular, considering manufacture, supply and use of the bioartificial kidney, there should be a need for a bioartificial kidney capable of retaining the renal function over several weeks of longer.

By the way, a drug administered to a living body demonstrates an action in vivo, and then excreted from blood through the proximal tubule into urine. Hence, the proximal tubule cell is susceptible to drug, and may be damaged by toxicity of the drug. It is therefore very beneficial in new drug development to develop a module for predicting toxicity of candidate substance against the proximal tubule epithelial cell, and drug metabolism. The aforementioned hybrid module, composed of the polymer membrane and the proximal tubule epithelial cell, would be suitably applicable also as such drug evaluation module.

Manufacture of the bioartifical kidney or the drug evaluation module requires to culture a large amount of proximal tubule epithelial cells used for these devices. Meanwhile, not only the proximal tubule epithelial cell, but also pluripotent cell such as embryonic stem cell (ES cell) and induced pluripotent stem cell (iPS cell), having been under recent active research and development, are required to be cultured in large quantities. Patent literature 1 discloses, as a technique for culturing a large amount of cells, a culture apparatus having a culture tank that houses a cell-containing culture medium, and a stirring blade arranged at the bottom of the culture tank. The culture apparatus is a spinner flask devised to reduce shear stress applied to cells, with a sophisticated shape of stirring blade.

Patent document 1: WO2013/187359

The present inventors made thorough investigations into stirred culture of proximal tubule epithelial cell and pluripotent stem cell using a spinner flask, and arrived at a novel culture technique capable of culturing large amounts of these cells that retain good conditions of their performances and properties.

SUMMARY OF THE INVENTION

The present invention was conceived in consideration of such circumstances, one of objects of which is to provide a technique for culturing a large amount of cells that retain good conditions of their performances and properties.

Aimed at solving the aforementioned problem, one embodiment of the present invention relates to a method of culturing cells. The method of culturing cells includes culturing the cell in a cell suspension under repetitive cycles of stirring and rest, while keeping the cell non-adherent to a culture vessel, so as to form at least one aggregate of the cell.

Another embodiment of the present invention relates to a method of manufacturing a cell support complex. The method includes: coating a coating agent that contains one or more components selected from the group consisting of laminin molecule, basement membrane matrix mixture, collagen molecule and fragment of any of these components, over at least a part of a base; deaggregating the aggregate formed by the method of culturing cells described in any one of aforementioned embodiments into the discrete cultured cells; and seeding the cultured cells on the base coated with the coating agent, and culturing the cultured cells on the base to thereby form a monolayer structure of the cultured cells.

Yet another embodiment of the present invention relates to a cultured cell. The cultured cell is manufactured by culturing the cell in a cell suspension under repetitive cycles of stirring and rest while keeping the cell non-adherent to a culture vessel, so as to form at least one aggregate of the cell.

Yet another embodiment of the present invention relates to a cell support complex. The cell support complex includes: a base; a coating agent layer containing one or more components selected from the group consisting of laminin molecule, basement membrane matrix mixture, collagen molecule and fragment of any of these components, formed so as to cover at least a part of the base; and the cultured cell described in the aforementioned embodiment, adhered to the base while placing the coating agent layer in between.

Note that also free combinations of these constituents, and any of the constituents and expressions exchanged among the method, device and system, are valid as the embodiments of the present invention.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 1A and FIG. 1B are drawings schematically illustrating structures of cell support complexes according to reference examples.

FIG. 6 is a chart summarizing time-dependent changes in gene expression levels in cells obtained after adhesion culture.

FIG. 7 is a chart summarizing time-dependent changes in gene expression levels in cells that compose an aggregate.

FIG. 8 is a chart summarizing time-dependent changes in gene expression levels in cells that compose an aggregate.

FIG. 10 is a chart summarizing gene expression levels in cells obtained after continuous stirred culture of the aggregates.

FIG. 12 is a chart summarizing presence or absence of aggregate in the intermittent stirred culture under various conditions.

FIG. 13 is a chart summarizing gene expression levels in cells obtained after intermittent stirred culture with varied rest time.

FIG. 14 is a chart summarizing gene expression levels in cells obtained after stirred culture with varied stirring speed.

DETAILED DESCRIPTION OF THE INVENTION

Figure 2A:
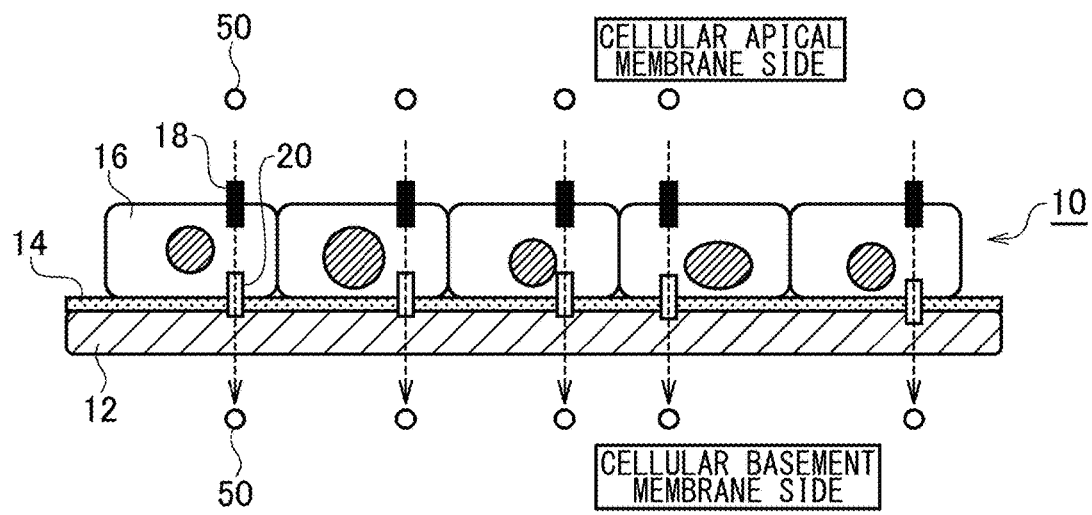
FIG. 2A to FIG. 2C are drawings schematically illustrating cultured cells according to an embodiment, and structures of cell support complexes having the cultured cells.

One embodiment of the present invention relates to a method of culturing cells. The method of culturing cells includes culturing the cell in a cell suspension under repetitive cycles of stirring and rest, while keeping the cell non-adherent to a culture vessel, so as to form an aggregate of the cell. This embodiment enables culturing of a large amount of cells that suitably retain their performances and properties.

The aforementioned embodiment may further include, subsequent to the step of culturing the cell under repetitive cycles of stirring and rest, culturing the cell in a state of aggregate, with the cell suspension kept stirred. Rest time may be longer than 5 minutes and shorter than 480 minutes. The culture vessel in which the cell suspension is stirred has a stirring blade, which may rotate at a speed faster than 20 rpm. The shear stress loaded on the cell by stirring may be $0.3 \text{ N/m}^2$ or smaller in absolute value. Culture period of the cell may be 5 days or longer and 14 days or shorter. The number of cells composing the aggregate may be 500 or larger and 5000 or smaller. Size of the aggregate may be 100 µm or larger and 350 µm or smaller.

Another embodiment of the present invention relates to a method of manufacturing a cell support complex. The method includes: coating a coating agent that contains one or more components selected from the group consisting of laminin molecule, basement membrane matrix mixture, collagen molecule and fragment of any of these components, over at least a part of a base; deaggregating the aggregate formed by the method of culturing cells described in any one of aforementioned embodiments into the discrete cultured cells; and seeding the cultured cells on the base coated with the coating agent, and culturing the cultured cells on the base to thereby form a monolayer structure of the cultured cells.

Yet another embodiment of the present invention relates to a cultured cell. The cultured cell is manufactured by culturing the cell in a cell suspension under repetitive cycles of stirring and rest while keeping the cell non-adherent to a culture vessel, so as to form an aggregate of the cell.

Yet another embodiment of the present invention relates to a cell support complex. The cell support complex includes: a base; a coating agent layer containing one or more components selected from the group consisting of laminin molecule, basement membrane matrix mixture, collagen molecule and fragment of any of these components, formed so as to cover at least a part of the base; and the cultured cell described in the aforementioned embodiment, adhered to the base while placing the coating agent layer in between.

The present inventors examined a technique of culturing renal cells, and came to understand as below. Renal cells such as proximal tubule epithelial cell, when isolated from kidney by enzymatic digestion (primary cultured cells), will dedifferentiate and gradually lose the function due to loss of in vivo environment, and due to a culture environment such as two-dimensional culture in a petri dish. Hence, a simple culture of the renal cells will only result in proliferation of cells with poor physiological functions. A bioartificial kidney, when manufactured using the dedifferentiated cell, would have only an insufficient level of reabsorption of active ingredients in plasma. In addition, a drug evaluation module, when manufactured using the dedifferentiated cell, would not demonstrate highly accurate pharmacokinetics or toxic reaction.

In contrast, the present inventors found that a specific culture can restore physiological functions of the dedifferentiated renal cells, and by which a large amount of renal cells even with better physiological functions are obtainable.

Proximal tubule epithelial cells, when isolated from kidney, cannot keep the original columnar cell structure, and deform into flat shape. Moreover, the proximal tubule epithelial cells, when seeded over a petri dish or an artificial membrane, will lose the monolayer epithelial structure, causing gaps among the cells, or stacking of the cells. These events can make the bioartificial kidney less effective to reabsorb the active ingredients. This can also degrade accuracy of the drug evaluation module. In contrast, the present inventors found a technique for forming a stable monolayer epithelial structure on the base, using proximal tubule epithelial cells with their physiological functions restored.

The present inventors additionally found that also pluripotent cells such as embryonic stem cell (ES cell) and induced pluripotent stem cell (iPS cell), are obtainable in large quantities with their pluripotency kept in good conditions, similarly by the specific culture. The embodiments were conceived on the basis of such contemplation.

The present invention will be explained below on the basis of preferred embodiments, referring to the attached drawings. The embodiments are merely illustrative, and are not restrictive about the invention. All features and combinations thereof described in the embodiments are not always necessarily essential to the present invention. All constituents, members and processes illustrated in the individual drawings will be given same reference numerals, so as to properly avoid redundant explanations. Reduced scales and shapes of the individual parts in the individual drawings are properly given for simplicity of explanation, and should not be interpreted restrictively unless otherwise specifically noted. Also not that ordinal terms "first", "second" and so on used in this patent specification and in claims do not represent any sequential order or importance, and are used only for discrimination of one structure from the other.

FIG. 1A and FIG. 1B are drawings schematically illustrating structures of cell support complexes according to reference examples. FIG. 1A illustrates a cell support complex using a well-known coating agent. FIG. 1B illustrates a cell support complex using no coating agent. As illustrated in FIG. 1A, a cell support complex 100a, obtained by seeding proximal tubule epithelial cells 106, over a base 104 such as an artificial membrane coated with a well-known general coating agent 102, has occasionally caused stacking of the proximal tubule epithelial cells 106, or gaps among the cells. Similarly as illustrated in FIG. 1B, also a cell support complex 100b, obtained by seeding the proximal tubule epithelial cells 106, over the base 104 having no coating agent 102 coated thereon, has suffered from such stacking of the proximal tubule epithelial cells 106, or gaps among the cells.

A region where the proximal tubule epithelial cells 106 mutually stack inhibits transfer of active ingredients from the cellular apical membrane side to the cellular basement membrane side, by way of a transporter (arrow P). There also possibly occurs a concentration-dependent mass transfer within the gaps between the neighboring proximal tubule epithelial cells 106, through the base 104 (arrow Q).

Figure 2B:
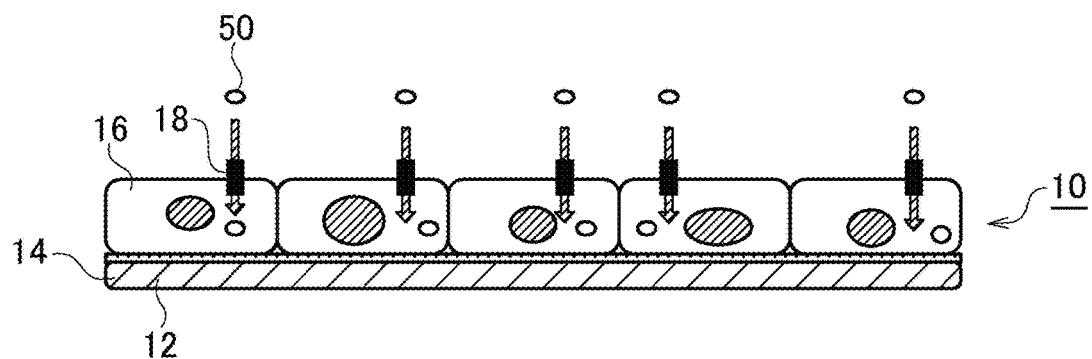
Figure 2C:
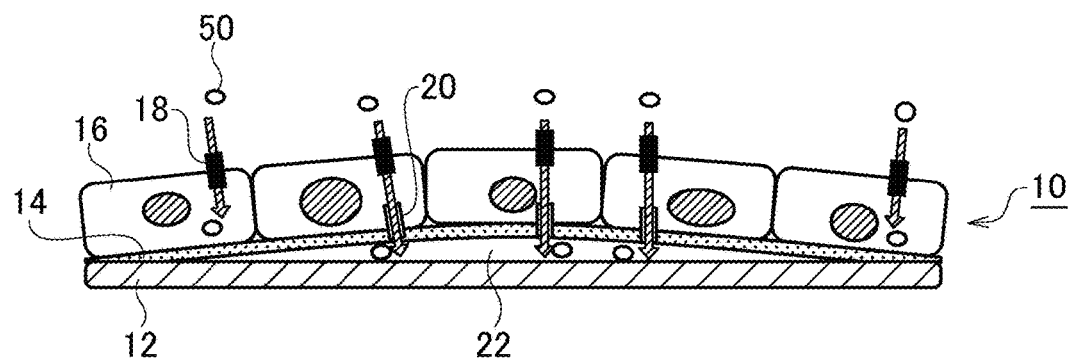

FIGS. 2A to 2C are drawings schematically illustrating cultured cells according to the embodiment, and structures of cell support complexes having the cultured cells. FIG. 2A illustrates a cell support complex using a water-permeable base, in other words, a base with a relatively high water permeability. FIG. 2B illustrates a cell support complex using a water-impermeable base, in other words, a base with a relatively low water permeability, viewed after a short lapse of time. FIG. 2C illustrates a cell support complex using a water-impermeable base, viewed after a long lapse of time.

A cell support complex 10 has a base 12, a coating agent layer 14, and cultured cells 16.

Base

The base 12 is typically composed of an artificial material. As illustrated in FIG. 2A, the base 12 is permeable to water and various ions. The base 12 is also preferably permeable to saccharides and low-molecular-weight proteins. The cell support complex 10 having such base 12 is applicable, for example, to bioartificial kidney. Active ingredient 50 that resides on the cellular apical membrane side passes through the cell support complex 10, by way of a transporter 18 on the cellular apical membrane side, a transporter 20 on the cellular basement membrane side, both owned by each cultured cell 16, and the base 12, to thereby reach the cellular basement membrane side.

The base 12 is provided, for example, with holes for the purpose of making the base 12 permeable to various substances. The holes provided to the base 12 preferably have an average pore size of 5 μm or smaller. With the average diameter adjusted to 5 μm or smaller, the cultured cells 16 will be less likely to pass through the base 12. For the base 12, available for example is Transwell® (from Corning Inc.: average pore size=0.4 μm or 3.0 μm).

Alternatively as illustrated in FIG. 2B and FIG. 2C, the base 12 may be impermeable to water and various ions. The cell support complex 10 having such base 12 is applicable, for example, to a drug evaluation module used for evaluating drug metabolism (intake of drug by the cultured cells 16) and toxicity. A water-impermeable petri dish or well plate may be used for the base 12. The active ingredient 50 that resides on the cellular apical membrane side is incorporated, through the transporters 18 of the cultured cells 16, inside the cultured cells 16. Within a short lapse of time from the start of use, only a small amount of active ingredient 50 moves through the transporters 20 of the cultured cells 16 towards the cellular basement membrane side, so that the layer of the cultured cells 16 remains unchanged as illustrated in FIG. 2B. Meanwhile, after a long lapse of time, the amount of transfer of the active ingredient 50 through the transporters 20 will increase, but the active ingredient 50 cannot pass through the base 12, causing lift-up of the layer of the cultured cells 16 to form a dome 22, as illustrated in FIG. 2C.

Materials for composing the base 12 are exemplified by, but not specifically limited to, polystyrene, polycarbonate (PC), polyester (PET), polyester-based polymer alloy (PEPA), ethylene-vinyl alcohol copolymer (EVOH), polyethylene, polysulfone (PSf) and polyethersulfone (PES). The base 12 may have any shape exemplified by, but not specifically limited to, culture well plate; culture petri dish; artificial membranes such as hollow fiber membrane, Transwell® and flat sheet membrane; micro-channel chip; solid particle; and hollow particle.

Coating Agent Layer

The coating agent layer 14 is a layer formed of a coating agent. The coating agent layer 14 covers at least a part of the base 12. The coating agent layer 14 is fixed on the base 12, while adhering itself to the face of the base 12. The aforementioned "at least a part of the base 12" means, for example, that at least one face of the base 12 having a flat face or a curved face. For the base 12 in the form of flat plate, "at least a part of the base 12" typically means at least one of the principal faces of the flat plate. For the base 12 in the form of circular column, "at least a part of the base 12" means at least one of the inner face or the outer face of the circular column.

The coating agent contains one or more adhesion molecules selected from the group consisting of laminin molecule, basement membrane matrix mixture, collagen molecule, and fragment of either of them. With the coating agent layer 14 containing these adhesion molecule, the monolayer structure of the cultured cells 16 will be formed more reliably.

Laminin Molecule

Laminin molecule has a heterotrimer structure having one each of α chain, β chain and γ chain. At present, identified are five types of α chain, three types of β chain, and three types of γ chain. The laminin molecule has been known to form at least 12 types of isoform based on combinations of these chains. In this embodiment, the laminin molecule is one or more selected from laminin 111, laminin 211, laminin 221, laminin 311, laminin 332, laminin 421, laminin 511, laminin 521 and fragments of them.

The laminin molecule encompasses variants of laminin (modified laminins) having a predetermined modification group at one or more sites of the aforementioned isoforms. The variants also encompass gene recombinant, that is, protein derived from recombined gene and then mutated, partial protein of gene recombinant, and protein having peptide derived from gene recombinant.

Among from the isoforms of laminin molecule, more preferred are laminin 311, laminin 511 and laminin 521, for their electric resistance, which is an index of intercellular barrier function, higher than that of laminin 111. Laminin 511 and laminin 521 are more preferred also because of their cost lower than that of laminin 111.

Concentration of the laminin molecule in the coating agent, and the amount of adhesion of the laminin molecule on the base 12 are properly controlled, so that the cell support complex 10 can keep the performance over the period of practical use. The amount of adhesion of the laminin molecule may be controlled by adjusting the concentration of laminin molecule in the coating agent. The period of practical use of the cell support complex 10 is preferably two weeks or longer after the seeding of the cultured cells 16 on the base 12, which is more preferably three weeks or longer, and even more preferably four weeks or longer.

The amount of adhesion of the laminin molecule on the base 12 can be determined by any of methods known to those skilled in the art. For example, a coating agent containing the laminin molecule is coated over the base 12, and allowed to stand overnight at 4° C., to form the coating agent layer 14. The amount of laminin molecule adhered on the base 12 can be quantified by using, for example, 2-D Quant Kit (from GE Healthcare).

Laminin 111 is preferably used at a concentration of 3.0 µg/ml or above, so as to attain an amount of adhesion of approximately 0.15 $\mu g/cm^2$ or more. This successfully makes laminin 111 function more reliably as the adhesion molecule. This also makes it possible to keep the monolayer structure of the cultured cells 16 for approximately 15 days or longer. Laminin 111 is more preferably used at a concentration of 4.0 µg/ml or above, so as to attain an amount of adhesion of approximately 0.19 $\mu g/cm^2$ or more. This successfully keeps the monolayer structure of the cultured cells 16 for 28 days or longer.

Laminin 211 is preferably used at a concentration exceeding 8.0 µg/ml, so as to attain an amount of adhesion exceeding approximately 0.45 $\mu g/cm^2$. This successfully makes laminin 211 function more reliably as the adhesion molecule. This also makes it possible to keep the monolayer structure of the cultured cells 16 for approximately 15 days or longer. Laminin 211 is more preferably used at a concentration of 10 µg/ml or above, so as to attain an amount of adhesion of approximately 0.52 $\mu g/cm^2$ or more. This successfully keeps the monolayer structure of the cultured cells 16 for 28 days or longer.

Laminin 221 is preferably used at a concentration exceeding 8.0 µg/ml, so as to attain an amount of adhesion exceeding approximately 0.30 $\mu g/cm^2$. This successfully makes laminin 221 function more reliably as the adhesion molecule. This also makes it possible to keep the monolayer structure of the cultured cells 16 for approximately 15 days or longer. Laminin 221 is more preferably used at a concentration of 10 µg/ml or above, so as to attain an amount of adhesion of approximately 0.34 $\mu g/cm^2$ or above. This successfully keeps the monolayer structure of the cultured cells 16 for 18 days or longer.

Laminin 311 is preferably used at a concentration of 2.5 µg/ml or above, so as to attain an amount of adhesion of approximately 0.10 $\mu g/cm^2$ or more. This successfully makes laminin 311 function more reliably as the adhesion molecule. This also makes it possible to keep the monolayer structure of the cultured cells 16 for approximately 15 days or longer. Laminin 311 is more preferably used at a concentration of 4.0 µg/ml or above, so as to attain an amount of adhesion of approximately 0.15 $\mu g/cm^2$ or above. This successfully keeps the monolayer structure of the cultured cells 16 for 28 days or longer.

Laminin 332 is preferably used at a concentration of 8.0 µg/ml or above. This successfully makes laminin 332 function more reliably as the adhesion molecule. This also makes it possible to keep the monolayer structure of the cultured cells 16 for 15 days or longer. Laminin 332 is preferably used at a concentration of 10 µg/ml or more. This successfully keeps the monolayer structure of the cultured cells 16 for 18 days or longer.

Laminin 421 is preferably used at a concentration of 5.0 µg/ml or above, so as to attain an amount of adhesion of approximately 0.50 $\mu g/cm^2$ or more. This successfully makes laminin 421 function more reliably as the adhesion molecule. This also makes it possible to keep the monolayer structure of the cultured cells 16 for 15 days or longer. Laminin 421 is more preferably used at a concentration of 6.0 µg/ml or above, so as to attain an amount of adhesion of approximately 0.54 $\mu g/cm^2$ or more. This successfully keeps the monolayer structure of the cultured cells 16 for 18 days or longer. Laminin 421 is more preferably used at a concentration of 10 µg/ml or above, so as to attain an amount of adhesion of approximately 0.69 $\mu g/cm^2$ or more. This successfully keeps the monolayer structure of the cultured cells 16 for 28 days or longer.

Laminin 511 is preferably used at a concentration exceeding 8.0 µg/ml, so as to attain an amount of adhesion exceeding approximately 0.30 $\mu g/cm^2$. This successfully makes laminin 511 function more reliably as the adhesion molecule. This also makes it possible to keep the monolayer structure of the cultured cells 16 for approximately 15 days or longer. Laminin 511 is more preferably used at a concentration of 10 µg/ml or above, so as to attain an amount of adhesion of approximately 0.32 $\mu g/cm^2$ or more. This successfully keeps the monolayer structure of the cultured cells 16 for 18 days or longer.

Laminin 521 is preferably used at a concentration of 4.5 µg/ml or above, so as to attain an amount of adhesion of approximately 0.40 $\mu g/cm^2$ or more. This successfully makes laminin 521 function more reliably as the adhesion molecule. This also makes it possible to keep the monolayer structure of the cultured cells 16 for approximately 15 days or longer. Laminin 521 is more preferably used at a concentration of 5.0 µg/ml or above, so as to attain an amount of adhesion of 0.44 $\mu g/cm^2$ or more. This successfully keeps the monolayer structure of the cultured cells 16 for 28 days or longer.

Taking now the concentration of commercially available products of the individual laminin molecules into consideration, the concentration exceeding 100 µg/ml would make the process labor-consuming and costly. The concentration of the individual laminin molecules is therefore preferably 100 µg/ml or below.

When modified laminin is used as the laminin molecule, the modification group is for example a proliferation factor binding molecule or cell adhesion molecule. Also use of such modified laminin can demonstrate operations and effects same as those obtainable by using the unmodified laminin molecule.

Also fragment of the laminin molecule may be used as the adhesion factor to be contained in the coating agent. The fragment of laminin molecule is exemplified by an E8 region variant that contains a cell adhesion site (integrin binding site) in domain I, out of full-length laminin (denoted as laminin ***-E8). Such variant is exemplified by laminin 111-E8, laminin 211-E8, laminin 421-E8 and laminin 521-

E8. Molecular weight of each of these variants is approximately one fifth of that of the full-length laminin.

When the E8 region variant of laminin 511 (laminin 511-E8) is used as the fragment of laminin molecule, the concentration is preferably set to approximately 1.4 µg/ml or above and approximately 500 µg/ml or below, so as to attain the amount of adhesion of 0.15 µg/cm$^2$ or more and 31.18 µg/cm$^2$ or less, taking the concentration of a commercially available laminin 511-E8 (iMatrix-511: from Nippi, Inc.) into consideration. With the concentration preset to approximately 1.4 µg/ml or above, laminin 511-E8 can more reliably demonstrate the function as the adhesion molecule. Meanwhile, with the concentration of laminin 511-E8 preset to approximately 500 µg/ml or below, preparation of the coating agent will be prevented from becoming difficult. This also successfully keeps the monolayer structure of the cultured cells 16 for 28 days or longer. Laminin 511-E8 is more preferably used at a concentration of approximately 2.5 µg/ml or above and approximately 50 µg/ml or below, so as to attain an amount of adhesion of approximately 0.21 µg/cm$^2$ or more and 6.21 µg/cm$^2$ or less.

The fragment of laminin molecule applicable here includes not only E8 region variant, but also laminin peptide having cell adhesion activity, or synthetic peptide representing the cell adhesion active site only. Such laminin peptide is exemplified by YIGSR-containing peptide derived from domain III in β chain, PDSGR-containing peptide derived from domain III in β chain, RYVVLPR-containing peptide derived from domain III in β chain, RGD-containing peptide derived from domain III in α chain, KAFDITYVRLKF-containing peptide derived from domain I in γ chain, IKVAV-containing peptide derived from domain I in α chain, and LRE-containing peptide derived from domain I in β chain. The laminin peptide is used at a concentration of approximately 0.5 to approximately 500 µg/ml. Size of the fragment of laminin molecule is not specifically limited.

Use of the fragment of laminin molecule, having smaller molecular weight than the full-length laminin has, can make the coating more stable. This also makes the coating easier in micro areas. This also suppresses the coating from being mottled, since the adhesion molecule becomes less likely to aggregate. Hence the monolayer structure of the cultured cell 16 is suppressed from becoming non-uniform. Use of the fragment of laminin molecule also enables coating of the adhesion molecule at high concentration and high density. Recombinant protein will enjoy higher production efficiency and purification efficiency, as its molecular weight decreases. Hence, use of the fragment of laminin molecule can further reduce manufacturing cost of the cell support complex 10.

Each of the full-length laminin molecule and the fragment of laminin molecule may contain a plurality of isoforms mixed therein. Alternatively, the full-length laminin molecule and the fragment of laminin molecule may be used in a mixed manner. Alternatively, a plurality of coating agents that contain different kinds of the full-length laminin and/or fragment of laminin molecule may be coated over the base 12, to thereby stack a plurality of coating agent layers 14 that contain different kinds of laminin.

Basement Membrane Matrix Mixture

The basement membrane matrix mixture is a mixture of extracellular matrix protein extracted from murine sarcoma. The basement membrane matrix mixture contains laminin, collagen IV and entactin as the principal constituents. The basement membrane matrix mixture is exemplified by Matrigel® (registered trademark: from Corning Inc.).

Matrigel® is a soluble basement membrane matrix, extracted from Engelbreth-Holm-Swarm (EHS) murine sarcoma that abundantly contains extracellular matrix protein. In this embodiment, Matrigel® not only includes normal Matrigel® that contains a growth factor, but also Matrigel® having the growth factor reduced therein (Growth Factor Reduced Matrigel® Matrix). In the description below, normal Matrigel® will be referred to as a first Matrigel®, and growth factor-reduced Matrigel® will be referred to as a second Matrigel®. The first Matrigel® and the second Matrigel® are available, for example, from Corning Inc. The first Matrigel® contains approximately 56% of laminin, approximately 31% of collagen IV, and approximately 8% of entactin. Meanwhile, the second Matrigel® contains approximately 61% of laminin, approximately 30% of collagen IV, and approximately 7% of entactin.

As the basement membrane matrix mixture, also employable is a mixture that contains laminin, collagen IV and entactin mixed according to a mass ratio of (ca. 56 to ca. 61):(ca. 30 to ca. 31):(ca. 7 to ca. 8).

Concentration of the basement membrane matrix mixture in the coating agent, and the amount of adhesion of the basement membrane matrix mixture on the base 12 are properly controlled, so that the cell support complex 10 can keep the performance over the period of practical use. The amount of adhesion of the basement membrane matrix mixture may be controlled by adjusting the concentration of basement membrane matrix mixture in the coating agent.

The first Matrigel® is more preferably used at a concentration exceeding 0 µg/ml and 3000 µg/ml or below, so as to attain an amount of adhesion exceeding 0 µg/cm$^2$ and approximately 34.85 µg/cm$^2$ or less. With the concentration of the first Matrigel® preset to 3000 µg/ml or below, the cultured cell 16 will become less likely to aggregate due to gelation of the first Matrigel®. The first Matrigel® is more preferably used at a concentration of 5.0 µg/ml or above and 2000 µg/ml or below, so as to attain an amount of adhesion of approximately 0.5 µg/cm$^2$ or more and approximately 25 µg/cm$^2$ or less. The first Matrigel® is even more preferably used at a concentration of 5.0 µg/ml or above and 1000 µg/ml or below, so as to attain an amount of adhesion of approximately 0.5 µg/cm$^2$ or more and 16.04 µg/cm$^2$ or less. This successfully keeps the monolayer structure of the cultured cells 16 for 28 days or longer.

The second Matrigel® is preferably used at a concentration exceeding 20 µg/ml and 1000 µg/ml or below, so as to attain an amount of adhesion exceeding 1.36 µg/cm$^2$ and 30.6 µg/cm$^2$ or less. With the concentration controlled exceeding 20 µg/ml, the second Matrigel® can more reliably demonstrate the function as the adhesion molecule. With the concentration of the second Matrigel® preset to 1000 µg/ml or below, the cultured cell 16 will become less likely to aggregate due to gelation of the second Matrigel®. The second Matrigel® is more preferably used at a concentration of 40 µg/ml or above and 1000 µg/ml or below, so as to attain an amount of adhesion of 3.15 µg/cm$^2$ or more and 30.6 µg/cm$^2$ or less. This successfully keeps the monolayer structure of the cultured cells 16 for 28 days or longer.

Also fragment of the basement membrane matrix mixture may be used as the adhesion factor to be contained in the coating agent. The fragment of the basement membrane matrix mixture means a fragment having mixed therein at least one of laminin fragment, collagen IV fragment and entactin fragment. A plurality of types of each of the full-length body and fragment of the basement membrane matrix mixture may be mixed and used. Alternatively, the full-length body and the fragment may be used in a mixed manner. Alternatively, a plurality of coating agents that contain different kinds of the full-length body and/or fragment may be coated over the base 12, to thereby stack a plurality of coating agent layers 14 that contain different kinds of mixture species.

Collagen Molecule

The collagen molecule is exemplified by collagen I and collagen IV. They are commercially available from Nitta Gelatin Inc. Concentration of the collagen molecule in the coating agent, and the amount of adhesion of the collagen molecule on the base 12 are properly controlled, so that the cell support complex 10 can keep the performance over the period of practical use. The amount of adhesion of the collagen molecule may be controlled by adjusting the concentration of collagen molecule in the coating agent.

Collagen I is preferably used at a concentration exceeding 750 μg/ml and 3000 μg/ml or below, so as to attain an amount of adhesion exceeding approximately 50 μg/cm$^2$ and 138 μg/cm$^2$ or less. With the concentration controlled exceeding 750 μg/ml, collagen I can more reliably demonstrate the function as the adhesion molecule. Meanwhile, with the concentration of collagen I preset to 3000 μg/ml or below, difficulty in uniform coating of the coating agent, due to high viscosity of collagen I, will more reliably be avoidable. This also successfully keeps the monolayer structure of the cultured cells 16 for 15 days or longer. The collagen I is more preferably used at a concentration of 1000 μg/ml or above and 3000 μg/ml or below, so as to attain an amount of adhesion of 65.4 μg/cm$^2$ or more and 138 μg/cm$^2$ or less. This successfully keeps the monolayer structure of the cultured cells 16 for 28 days or longer.

Collagen IV is preferably used at a concentration exceeding 500 μg/ml and 3000 μg/ml or below, so as to attain an amount of adhesion exceeding 19.2 μg/cm$^2$ and 121 μg/cm$^2$ or less. With the concentration controlled exceeding 500 μg/ml, collagen IV can more reliably demonstrate the function as the adhesion molecule. Meanwhile, with the concentration of collagen IV preset to 3000 μg/ml or below, difficulty in uniform coating of the coating agent, due to high viscosity of collagen IV, will more reliably be avoidable. This also successfully keeps the monolayer structure of the cultured cells 16 for 15 days or longer. The collagen IV is more preferably used at a concentration of 750 μg/ml or above and 3000 μg/ml or below, so as to attain an amount of adhesion of approximately 25 μg/cm$^2$ or more and 121 μg/cm$^2$ or less. This successfully keeps the monolayer structure of the cultured cells 16 for 28 days or longer.

Also fragment of the collagen molecule may be used as the adhesion factor to be contained in the coating agent. A plurality of types of each of the full-length body and fragment of the collagen molecule may be mixed and used. Alternatively, the full-length body and the fragment may be used in a mixed manner. Alternatively, a plurality of coating agents that contain different kinds of the full-length body and/or fragment may be coated over the base 12, to thereby stack a plurality of coating agent layers 14 that contain different kinds of collagen species.

The aforementioned laminin molecule, the basement membrane matrix mixture, the collagen molecule, and the fragments thereof may be used independently, or two or more kinds of them may be used in a mixed manner. The coating agent may also have mixed therein other adhesion protein such as gelatin.

Cultured Cell

The cultured cells 16 adhere to the base 12, while placing the coating agent layer 14 in between. The cultured cells 16 are adhered to the base 12 with the aid of the coating agent layer 14. Each cultured cell 16 has the transporter 18 on the cellular apical membrane side, and the transporter 20 on the cellular basement membrane side.

The cultured cells 16, when derived from renal cells for example, are manufactured by culturing the cells in a cell suspension under repetitive cycles of stirring and rest while keeping the cells non-adherent to a culture vessel, so as to form at least one aggregate of the cells. The cultured cells 16 necessarily retain the physiological functions, when intended for use on the cell support complex 10. Meanwhile, renal cells will dedifferentiate and loose their physiological functions when cultured under an environment different from the in vivo environment. In contrast, the renal cells, when cultured under intermittent stirring while keeping them non-adherent to the culture vessel, can form at least one aggregate, and thereby the declined physiological functions of the renal cells can be restored. Note that even a slight improvement of the physiological functions, once declined by culture, is encompassed in "restoration" in this embodiment. "Stirring" means moving (displacement) of the cells in the cell suspension, and includes shaking of the cell suspension.

More specifically, the renal cells form at least one aggregate, when cultured in a suspended state while intermittently stirring the cell suspension (medium, in other words). For example, the aggregate of the renal cells is formed on the first day (that is, within 24 hours). The subsequent culturing of the renal cells in the form of aggregate can restore the physiological functions of the renal cells. Hence, the cultured cells 16 are those having the physiological functions of the renal cells. Method of culturing the cells will be detailed later. Note that "suspended" means a state of the cells non-adherent to the wall of the culture vessel. Hence, "suspended" encompasses a state where the cells might be brought into contact with the wall of the culture vessel, but can easily be separated from the wall, typically with the aid of convection of the medium.

The renal cells from which the cultured cell 16 are derived include renal cells derived from tissue, and renal cells derived from iPS cell or ES cell. The renal cells include, for example, at least one of epithelial cells from the proximal tubule system, distal tubule system and collecting duct system. More specifically, the renal cells are exemplified by human proximal tubule epithelial cell, human distal tubule epithelial cell and human collecting duct epithelial cell which are collected and isolated from kidney; and proximal tubule epithelial cell, distal tubule epithelial cell and collecting duct epithelial obtained by inducing differentiation from human iPS cells or human ES cells. The renal cells are more preferably proximal tubule epithelial cell. The renal cells also include immortalized cell of the aforementioned renal cells, established cell line (HK-2 cell, etc.), transformed cell having incorporated therein a gene for expressing protein such as a specific transporter, and renal progenitor cell. The renal cells employable here may alternatively be cells derived from other animals (MDCK cell, LLC-PK1 cell, JTC-12 cell, etc.), in place of the human renal cells.

The cultured cells 16 form a confluent monolayer over the base 12, substantially without causing stratification. The term "substantially" means that the monolayer structure is maintained enough to a degree that efficiency of mass transfer will not be decline by stratification, and does not mean that the stratification does not occur at all. The term "confluent" means a state that an area occupied by the cultured cells 16 accounts for 100% of the total culture surface, that is, the cells proliferate so as to completely cover the culture surface without causing gaps. Whether the state of the cells is confluent or not may be determined easily by the skilled person.

Method of Culturing Cells and Method of Manufacturing Cell Support Complex

FIG. 3A to FIG. 3D and FIG. 4A to FIG. 4C are stepwise drawings illustrating the method of culturing the cells and the method of manufacturing the cell support complex according to the embodiment. The method of culturing the cells of this embodiment includes culturing the cells in a cell suspension under repetitive cycles of stirring and rest while keeping the cells non-adherent to a culture vessel, so as to form at least one aggregate of the cell. The method of culturing enables manufacture of the cultured cells 16 that retain the physiological functions.

Moreover, the method of manufacturing a cell support complex includes:

deaggregating the aggregate 30 of the cultured cells 16 formed by the method of culturing cells according to this embodiment into the discrete cultured cells 16;

coating a coating agent over at least a part of the base 12; and seeding the cultured cells 16 on the base 12 coated with the coating agent, and culturing the cultured cells 16 over the base 12 to thereby form a monolayer structure of the cultured cell 16.

Figure 3A:
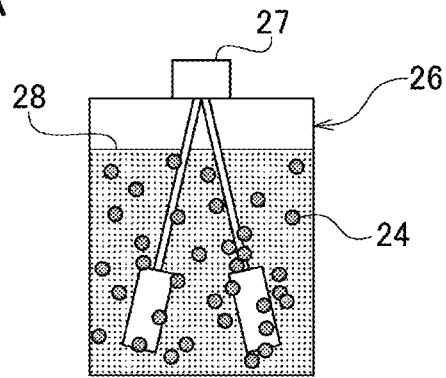
FIG. 3A to FIG. 3D are stepwise drawings illustrating a method of culturing cells and a method of manufacturing a cell support complex according to an embodiment.

More specifically, as illustrated in FIG. 3A, renal cells 24 are seeded in a culture vessel 26. The culture vessel 26 is a so called spinner flask, having a stirring blade 27 used for stirring the cell suspension. As the culture vessel 26, employable is a spinner flask, large stainless steel culture tank, cell culture bottle, cell culture bag and so forth, all being allowed for stirred culture (including shaking culture). To the culture vessel 26, a medium 28 is added. As the medium 28, any of known media is applicable. For culture of proximal tubule cells, available are REGM™ (from Lonza Inc.), EpiCM (from ScienCell Research Laboratories, Inc.), and Keratinocyte SFM (from Life Technologies Corporation), for example. Any of known materials necessary for culturing cells may be used.

Figure 3B:
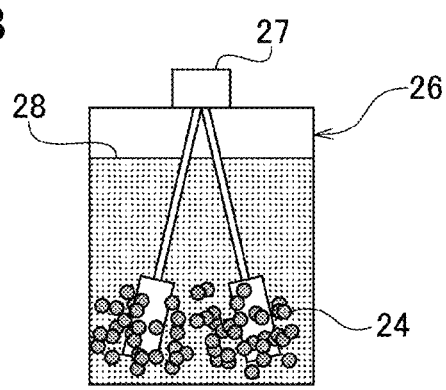

Next, as illustrated in FIG. 3B, the renal cells 24 are rested for a predetermined duration of time, before rotating the stirring blade 27. The rest time is typically longer than 5 minutes and shorter than 600 minutes. The renal cells 24, immediately after seeded in the culture vessel 26, are in a discrete state causing no adhesion with other cells. Rotation of the stirring blade 27 in this state tends to increase shear stress or damage applied to the renal cells 24. The rest time before stirring can promote mutual adhesion of the renal cells 24. This can moderate the load applied to the renal cells 24, and can promote subsequent formation of the aggregate 30.

Figure 3C:
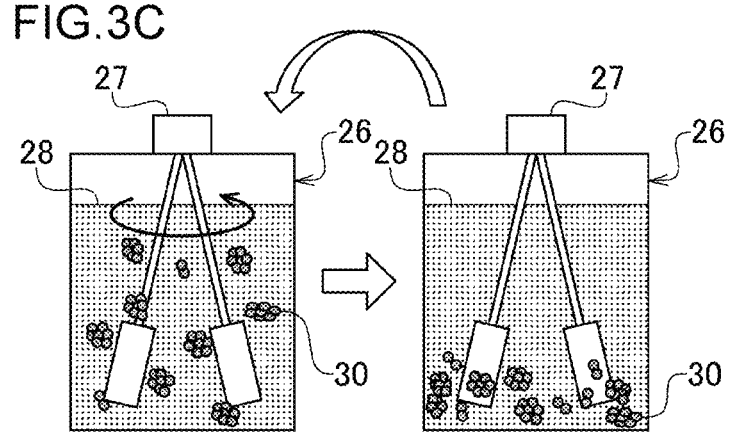

Next, the renal cells 24 are cultured while repeating, as illustrated in FIG. 3C, cycles of stirring (left in FIG. 3C) and rest (right in FIG. 3C) of the medium 28 containing the renal cells 24, that is, the cell suspension, by intermittently rotating the stirring blade 27. The cycle of stirring and rest is preferably repeated twice or more times. The renal cells 24 are now cultured in a suspended state, non-adherent to the culture vessel 26.

During the rest of cell suspension, the renal cells 24 precipitate and mutually adhere, to form the aggregate 30. During the repeated rest periods, the aggregate 30 gradually grows. During stirring of the cell suspension, the renal cells 24 are kept floated. Hence, the renal cells 24 are mutually brought into contact only within a short time, instead being exposed to shear stress. This inhibits mutual adhesion of the renal cells 24, and suppresses the aggregate 30 from growing. Mutual adhesion of the renal cells 24 include mutual adhesion of discrete renal cells 24, and adhesion of the renal cell 24 in the aggregate 30 and a discrete renal cell 24 (that is, adhesion of the renal cell 24 to the already formed aggregate 30).

Hence, repetition of the cycles of stirring and rest of the cell suspension makes it possible to form a large amount of aggregates 30 at a time, and to control the size of each aggregate 30. Such repetition of stirring and rest, or the intermittent stirring step, is carried out during a period of time typically one hour or longer and 10 hours or shorter. With the intermittent stirring step carried out for one hour or longer, the aggregate 30 may be formed more reliably. Meanwhile, with the intermittent stirring step carried out for 10 hours or shorter, the aggregate 30 is reliably prevented from becoming too large.

The aggregate 30, if becoming too large, will make the cells deep inside of the aggregate 30 more likely to cause undernutrition or hypoxia, possibly promoting cell death. This could also make it difficult to uniformalize performance of the cultured cell 16, and could degrade the yield of cells desired to be obtained. The excessively large aggregate 30 also promotes mutual adhesion of the aggregates 30, making it yet more difficult to obtain the uniform cultured cell 16.

The number of renal cells 24 composing the aggregate 30 obtained in the intermittent stirring step is preferably 500 or larger and 5000 or smaller. Size of the aggregate 30 is preferably 100 μm or larger and 350 μm or smaller. The number of cells composing the aggregate 30 correlates with the size. The size of aggregate 30, having approximately 500 or more and 5000 or less constitutive cells, measures approximately 100 μm or larger and 350 μm or smaller. The size of aggregate 30 is defined by a maximum width of the aggregate 30. That is, the size of aggregate 30 is given by length of the longest straight line, among from straight lines that connect two points on the outer edge of the aggregate 30. Note since the aggregate 30 is nearly spherical, so that the size of aggregate 30 will be referred to as the diameter of aggregate 30 hereinafter for convenience's sake.

The aggregate 30, when preset to have a number of constitutive cells of 500 or larger, or a diameter of 100 μm or larger, will be more reliably prevented from being sucked together with an old medium, for example when the medium is exchanged. Meanwhile, with the number of constitutive cells preset to 5000 or smaller, or with the diameter preset to 350 μm or smaller, the cultured cells 16 that retain further better physiological functions are obtainable. The number of constitutive cells and the diameter of the aggregate 30 can be controlled by adjusting the cell density in the culture vessel 26. The cell density is typically 5000 cells/ml or above and 500000 cells/ml or below. With the cell density preset to 5000 cells/ml or above, the renal cells 24 can be brought into mutual contact more reliably during rest. Meanwhile, with the cell density preset to 500000 cells/ml or below, the renal cells 24 are prevented from being brought into excessive contact with each other, and thereby the aggregates 30 can be suppressed from becoming too large, and from adhering with each other.

During stirring of the cell suspension, rotating speed of the stirring blade 27 is preferably faster than 20 rpm, and more preferably 30 rpm or faster. This can reliably suspend the precipitated renal cells 24 and the aggregates 30. As a consequence, the aggregates 30 can be suppressed from becoming excessively large. The rotating speed of the stirring blade 27 is preferably 100 rpm or slower, and more preferably 75 rpm or slower. Hence, the renal cells 24 can be prevented from being excessively damaged due to stirring of the cell suspension.

The rest time in the intermittent stirring step is preferably longer than 5 minutes and shorter than 480 minutes. With the rest time preset to longer than five minutes, the renal cells 24 can be mutually adhered more reliably, and thereby the aggregate 30 can be formed more reliably. Meanwhile, with the rest time preset to shorter than 480 minutes, the aggregate 30 is prevented from becoming excessively large due to excessive aggregation of the renal cells 24, and the aggregates 30 are prevented from adhering with each other more reliably. The rest time is more preferably 10 minutes or longer and 240 minutes or shorter, even more preferably 10 minutes or longer and shorter than 60 minutes, and yet more preferably 10 minutes or longer and 30 minutes or shorter.

The stirring time in the intermittent stirring step is preferably 1 minute or longer and 30 minutes or shorter. With the stirring time preset to one minute or longer, the renal cells 24 can be suspended and dispersed more reliably. Hence, the aggregates 30 can be more reliably suppressed from growing. Meanwhile, with the stirring time preset to 30 minutes or shorter, the renal cells 24 will be less likely to be damaged due to stirring of the cell suspension.

Figure 3D:
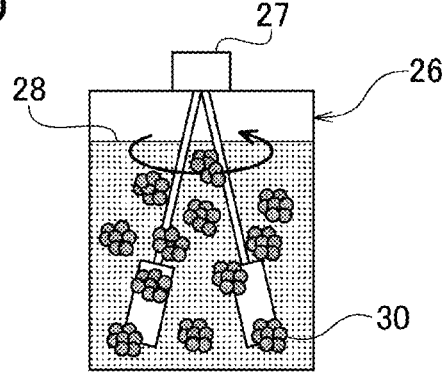

After completion of the intermittent stirring step, the cell suspension is kept stirred as illustrated in FIG. 3D, to thereby culture the renal cells 24 in the form of aggregate 30. Continuous stirring step is thus carried out. In the continuous stirring step, the renal cells 24 are inhibited from mutually adhering, in the same way as in the stirring period in the intermittent stirring step. Also mutual adhesion of the aggregates 30 is inhibited. Hence, with the intermittent stirring step followed by the continuous stirring step, it now becomes possible to restore the physiological functions of the renal cells 24 more reliably, while preventing the aggregate 30 from becoming too large. In the continuous stirring step, the medium is replaced as necessary. For example in the culture of proximal tubule cells, the medium 28 is changed every two to three days. In the culture of iPS cells, the medium 28 is changed every day. The medium may be changed by collecting the whole amount of medium containing the aggregates 30, and by allowing the aggregate 30 to precipitate by centrifugation.

In the intermittent stirring step and the continuous stirring step, shear stress loaded on the cell by stirring is preferably 0.3 N/m² or smaller in absolute value. A maximum value ($\zeta$max) of the shear stress may be calculated using the equation (1) below.

$$\zeta\text{max} = 5.33\rho(\varepsilon\nu)^{1/2} \quad (1)$$

In equation (1), where $\rho$ represents density of culture medium and $\nu$ represents viscosity of culture medium, and $\varepsilon$ is calculated using equation (2) below.

$$\varepsilon = N_p D_i^5 N^3 / V_d \quad (2)$$

In equation (2), $N_p$ represents non-dimensional power number, $D_i$ represents dissipation volume, N represents shape of stirring blade, and $V_d$ represents volume of distribution.

Maximum value and distribution of shear stress in the spinner flask may be determined alternatively by using fluid analysis software, while entering proper values for variants that include density of culture medium, viscosity of culture medium, shape of flask (aspect ratio), shape of stirring blade, diameter of stirring blade, wall conditions of flask, and number of rotation of stirring blade.

In a case where 80 ml of a medium was placed in a 100 ml spinner flask and stirred at a rotating speed of 75 rpm, the maximum value of shear stress was found to be 0.29 N/m². Similarly in a case where the medium was stirred at a rotating speed of 30 rpm, the maximum value of shear stress was found to be 0.12 N/m². The parameters were determined making reference to those described in Stem Cell Research (2013) 11, 1103-1116.

A period between the seeding into the culture vessel 26 (step illustrated in FIG. 3A) to the end of the continuous stirring step, that is the culture period of the renal cells 24, is preferably 5 days or longer (that is, 120 hours or longer). The culture period of the renal cells 24 is preferably 14 days or shorter (that is, 336 hours or shorter), and more preferably 10 days or shorter (that is, 240 hours or shorter). With the culture period preset to five days or longer, the cultured cells 16 that retain good conditions of their physiological functions are obtainable in a more reliable manner. Meanwhile, with the culture period preset to 14 days or shorter, the cultured cells 16 that strongly express the physiological functions are obtainable. With the culture period further preset to 10 days or shorter, the cultured cells 16 that more strongly express the physiological functions are obtainable. Culture conditions in the intermittent stirring step and the continuous stirring step relate to 37° C. and 5% $CO_2$, for example.

The culture vessel 26 is preferably treated by cell-repellent treatment or composed of a cell-repellent material. This can more reliably form the aggregates 30. The cell-repellent treatment is exemplified by a cell-repellent hydrogel coating, MPC (2-methacryloyloxyethyl phosphorylcholine) coating, PROTEOSAVE (registered trademark) SS coating, mirror polishing, etc. over the surface of vessel. The cell-repellent material is exemplified by glass. The cell-repellent material is also exemplified by polymer materials such as low density polyethylene, middle density polyethylene, polyvinyl chloride, polyethylene-vinyl acetate copolymer, poly(ethylene-ethyl acrylate) copolymer, poly(ethylene-methacrylate) copolymer, poly(ethylene-vinyl acetate) copolymer, and mixtures of two or more of these polymers.

Figure 4A:
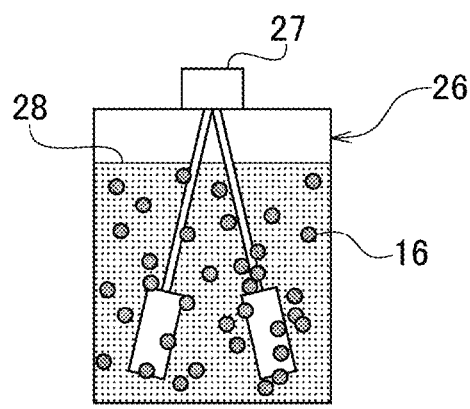
FIG. 4A to FIG. 4C are stepwise drawings illustrating the method of culturing cells and the method of manufacturing the cell support complex according to the embodiment.

Next, as illustrated in FIG. 4A, each aggregate 30 formed by the aforementioned method of culturing the cells is deaggregated into discrete cultured cells 16. Deaggregation of the aggregates 30 into the discrete cultured cells 16 may be carried out by enzymatic digestion of the aggregates 30 typically using trypsin/EDTA, Accutase®, EDTA or TrypLE™ Select. Concentration of the enzyme used for the digestion may be properly determined depending on kinds of the cultured cells 16. High enzyme concentration makes isolation of the cultured cells 16 easier, but would increase a risk of damaging cell surface proteins on the cultured cells 16. Hence, the enzyme concentration is preferably as low as possible.

Figure 4B:
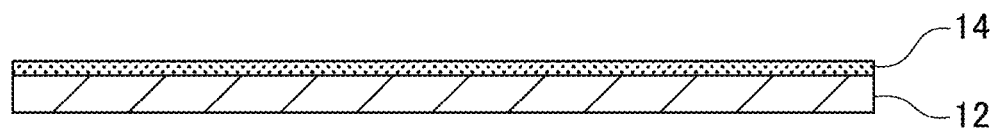

Next, as illustrated in FIG. 4B, the coating agent that contains one or more adhesion molecules selected from the group consisting of laminin molecule, basement membrane matrix mixture, collagen molecule, and fragment of either of them, is coated over at least a part of the base 12. The coating step forms the coating agent layer 14 on the face of the base 12. The isolation step of the cultured cells 16 and the coating step of the coating agent may be carried out independently. That is, either of these steps may precede to the other, or both steps are carried out concurrently.

Figure 4C:
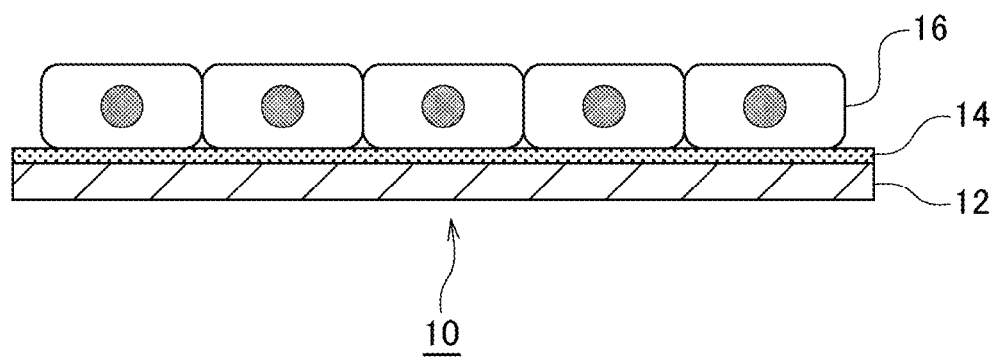

Then as illustrated in FIG. 4C, the cultured cells 16 are seeded over the base 12 having coated thereon the coating agent, and the cultured cells 16 are cultured over the base 12 to thereby form the monolayer structure of the cultured cells 16. The cultured cells 16 are seeded over the base 12, so as to adjust the cell density to approximately $1.0 \times 10^3$ to approximately $1.0 \times 10^5$ cells/cm$^2$. The culture period is typically one day or longer and 60 days or shorter. The cultured cells 16 proliferate up to a confluent state over the base 12, and keep the confluent state thereafter. The cultured cells 16 are cultured typically by using REGM™ (from Lonza Inc.) under conditions at 37° C. and 5% $CO_2$.

Note, in the step illustrated in FIG. 4C, the cultured cells 16 may be seeded over the base 12, by placing on the base 12 a cell suspension that contains the cultured cells 16 and a predetermined adhesion molecule. With the cell suspension having the predetermined adhesion molecule dispersed therein, mutual adhesion among the cultured cells 16, and adhesion between the cultured cells 16 and the base 12 are enhanced by aid of the adhesion molecule. This can stably keep geometry of the confluent monolayer of the cultured cells 16 (properly referred to as cell monolayer, hereinafter). The cell monolayer is formed typically within a day (that is, within 24 hours) after seeding of the cultured cells 16 over the base 12. The cell suspension may be rested or shaken for a predetermined length of time before placed on the base 12, in order to promote contact between the cultured cells 16 and the adhesion molecule. The length of time of rest or shaking is typically, but not specifically limited to, 30 minutes or shorter at room temperature or 37° C. In a case where the predetermined adhesive molecule is added in the cell suspension, the coating process illustrated in FIG. 4B is omissible. That is, the coating agent layer 14 is omissible from the finally obtainable cell support complex 10.

The cell suspension includes a medium. The medium employable here includes REGM™ (from Lonza Inc.), EpiCM (from ScienCell Research Laboratories, Inc.), Keratinocyte SFM (from Life Technologies Corporation), and StemFit® (from Ajinomoto Co., Inc.). Also any of known materials necessary for cell culture may be included in the cell suspension.

The adhesion molecule contained in the cell suspension contains one or more selected from the group consisting of fragment of laminin molecule (fragmented laminin), fragment of basement membrane matrix mixture (fragmented basement membrane matrix mixture), and complete basement membrane matrix mixture (full-length basement membrane matrix mixture).

Fragment of Laminin Molecule

The fragmented laminin in this embodiment is one or more kinds of fragments selected from complete laminins (full-length laminins) including laminin 111, laminin 211, laminin 221, laminin 311, laminin 332, laminin 421, laminin 511 and laminin 521. Note, as explained previously, the laminin molecule encompasses variants of laminin (modified laminins) having a predetermined modification group at one or more sites of the isoforms. The modification group is typically a growth factor binding molecule or a cell adhesion molecule.

The fragmented laminin is exemplified by an E8 region variant. Such fragmented laminin is exemplified by laminin 111-E8, laminin 211-E8, laminin 411-E8, laminin 421-E8, laminin 511-E8 and laminin 521-E8. The fragmented laminin includes not only E8 region variant, but also laminin peptide having cell adhesion activity, and synthetic peptide representing the cell adhesion active site only. Such laminin peptide is exemplified by YIGSR-containing peptide, PDSGR-containing peptide, RYVVLPR-containing peptide, RGD-containing peptide, KAFDITYVRLKF-containing peptide, IKVAV-containing peptide, and LRE-containing peptide.

Fragment or Complete Body of Basement Membrane Matrix Mixture

The full-length basement membrane matrix mixture from which the fragmented basement membrane matrix mixture is derived contains laminin, collagen IV and entactin as the principal constituents, as described previously. The fragmented basement membrane matrix mixture is a mixture having mixed therein at least one of laminin fragment, collagen IV fragment and entactin fragment. The basement membrane matrix mixture contains first Matrigel® which is normal Matrigel®, and second Matrigel® which is a growth factor-reduced Matrigel®. As the basement membrane matrix mixture, also employable is a mixture that contains laminin, collagen IV and entactin mixed according to a mass ratio of (ca. 56 to ca. 61):(ca. 30 to ca. 31):(ca. 7 to ca. 8).

The fragmented laminin and the fragmented basement membrane matrix mixture have molecular weights smaller than those of their complete bodies. The fragments can therefore enter finer regions. The adhesion molecule will become less likely to aggregate, making it possible to more uniformly disperse the adhesion molecule in the cell suspension. These can more stably keep the confluent monolayer of the cultured cells 16.

Only a single kind of the aforementioned laminin molecule fragment, fragment of basement membrane matrix mixture and complete body of basement membrane matrix mixture may be used independently, or two or more kinds may be used in a mixed manner. The fragmented laminin employable here may be a single kind of isoform, or may be a mixture of two or more isoforms. Similarly, the fragmented basement membrane matrix mixture and the full-length basement membrane matrix mixture employable here may be a single kind of them, or may be a mixture of two or more kinds of them.

Concentration of the adhesion molecule in the cell suspension is preferably 0.04 μg or above per unit area (1 cm$^2$) of the culture surface of the base 12, or 0.04 μg/cm$^2$ or above, even more preferably exceeding 0.22 μg/cm$^2$, and yet more preferably exceeding 0.66 μg/cm$^2$. With the concentration of adhesion molecule controlled to 0.04 μg/cm$^2$ or above, the adhesion molecule will more reliably demonstrate the functions, and the structure of cell monolayer will be maintained more reliably. Moreover, with the concentration of adhesion molecule preset exceeding 0.22 μg/cm$^2$, and even exceeding 0.66 μg/cm$^2$, the number of days over which the cell monolayer is maintained can be elongated.

With the concentration of adhesion molecule particularly exceeding 0.66 μg/cm$^2$, the structure of cell monolayer is maintained more reliably over a period of practical use of the cell support complex 10. The concentration of adhesion molecule is more preferably 1.97 µg/cm² or above. Hence, the period over which the cell monolayer is maintained can be made not shorter than the period of practical use of the cell support complex 10 in a more reliable manner. The concentration of adhesion molecule is typically 22 µg/cm² or below.

Apparatus Using Cell Support Complex

FIG. 5A to FIG. 5F are drawings schematically illustrating an exemplary application of the cell support complex according to the embodiment. Note that FIG. 5A to FIG. 5F illustrate a part of a structure having incorporated therein the cell support complex. The cell support complex 10 of this embodiment is applicable to various apparatuses.

Figure 5B:
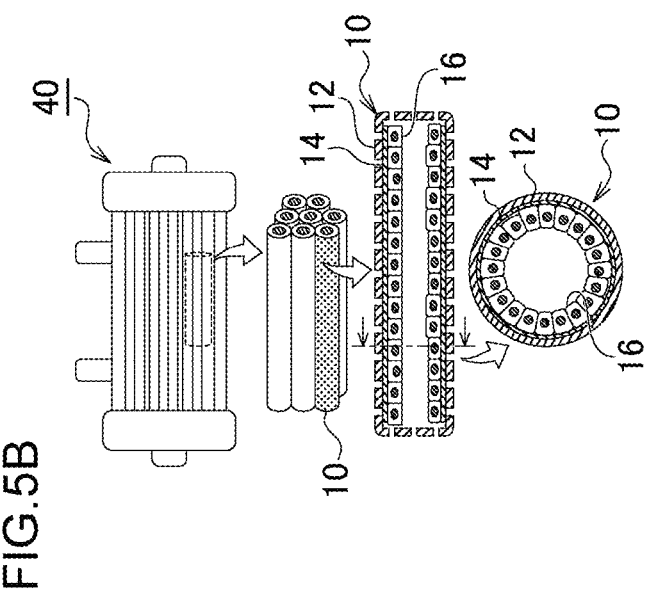
FIG. 5A to FIG. 5F are drawings schematically illustrating an exemplary application of the cell support complex according to the embodiment.
Figure 5A:
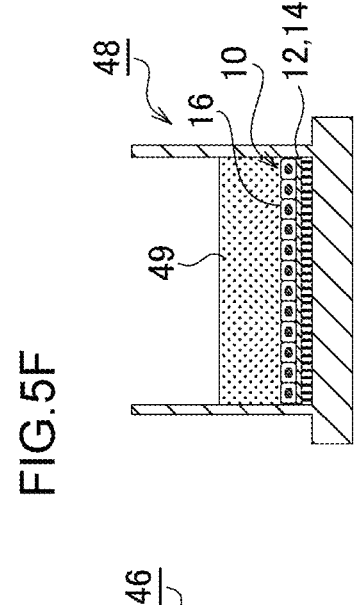

For example, FIG. 5A illustrates a first apparatus 34 equipped with Transwell® 32, having the cell support complex 10 incorporated therein. Transwell® 32, having a known structure, will not be detailed here. In the first apparatus 34, a first liquid 36 that contains a predetermined substance is fed on the side where the cultured cells 16 are arranged. The predetermined substance in the first liquid 36 is incorporated into the cultured cells 16, passes through the cell support complex 10, and moves to a second liquid 38 placed on the opposite side of the first liquid 36 while placing the cell support complex 10 in between. The first apparatus 34 is typically applicable to a drug evaluation module used for checking cell functions, and uptake and excretion of drug only with a microvolume of liquid.

FIG. 5B illustrates a second apparatus 40 having incorporated therein the cell support complex 10, in which hollow fiber membrane is used as the base 12. In the second apparatus 40, the coating agent layer 14 and the monolayer structure of the cultured cells 16 are formed in a tubular cavity of the hollow fiber membrane used as the base 12. Upon feeding of a liquid through the tubular cavity of the hollow fiber membrane, the second apparatus 40 can make the cultured cells 16 incorporate the predetermined substance in the liquid, and then move the substance outside of the tubular cavity of the hollow fiber membrane. The second apparatus 40 is applicable, for example, as a bioartificial kidney module that collects active ingredients out from plasma ingredients obtained after filtration through a blood filter.

Figures 5C, 5D, 5E:
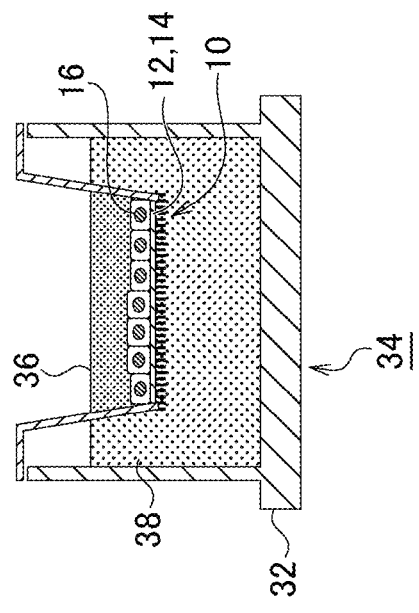

FIG. 5C illustrates a microchannel chip 42 having incorporated therein the cell support complex 10. In the microchannel chip 42, the base 12 composes a microchannel. The coating agent layer 14 and the monolayer structure of the cultured cells 16 are formed over the inner wall of the microchannel. In the microchannel chip 42, a microvolume of liquid is allowed to flow in the channel, that is, on the side the cultured cells 16 are arranged. The predetermined substance in the liquid is then incorporated into the cultured cells 16. The microchannel chip 42 is typically applicable to a drug evaluation module used for checking cell functions, and uptake and excretion of drug only with a microvolume of liquid.

FIG. 5D illustrates the cell support complex 10 composing a hollow microcarrier 44. FIG. 5E illustrates the cell support complex 10 composing a solid microcarrier 46. In the hollow microcarrier 44 and the solid microcarrier 46, the base 12 composes the carrier body. The coating agent layer 14 and the monolayer structure of the cultured cells 16 are formed over the outer face of the base 12. To the hollow microcarrier 44 and the solid microcarrier 46, a microvolume of liquid is fed on the side the cultured cells 16 are arranged. The predetermined substance in the liquid is then incorporated into the cultured cells 16. The hollow microcarrier 44 and the solid microcarrier 46 are typically applicable to a drug evaluation module used for checking cell functions, and uptake and excretion of drug only with a microvolume of liquid.

Figure 5F:
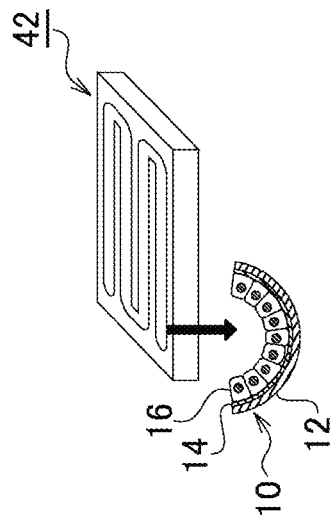

FIG. 5F illustrates a well plate 48 having incorporated therein the cell support complex 10. In the well plate 48, the cell support complex 10 is arranged on the bottom face of the well. In this arrangement, the cultured cells 16 are directed to the upside of the well. In the well plate 48, a microvolume of liquid 49 is dispensed in the well. The predetermined substance in the liquid 49 is then incorporated into the cultured cells 16. The well plate 48 is typically applicable to a drug evaluation module used for checking cell functions, and uptake and excretion of drug only with a microvolume of liquid. Note that, in place of the well plate 48, a culture dish (petri dish, etc.) may have incorporated therein the cell support complex 10.

The aforementioned module having incorporated therein the cell support complex 10 is used, while being properly enclosed in a cartridge just like the second apparatus 40.

As has been described above, the method of culturing the cells of this embodiment includes culturing the cells in a cell suspension under repetitive cycles of stirring and rest while keeping the cells non-adherent to a culture vessel, so as to form at least one aggregate of the cells. With the cell suspension cultured under intermittent stirring so as to keep the renal cells 24 in a suspended state, the renal cells 24 are made more likely to contact with each other during interruption of stirring of the cell suspension, and can be promoted to form the aggregate 30. A large amount of aggregates 30 can thus be formed at a time in a more reliable manner.

Formation of the aggregate 30 can restore the physiological functions of the renal cells 24 once declined by culture. The renal cells 24 when cultured in a discrete state under stirring tend to cause cell death, due to shear stress applied during stirring. In contrast, formation of the aggregate 30 can reduce the cell death. Hence, a large amount of cultured cells 16 can be obtained, with their physiological functions retained better than before. Moreover, by manufacturing the cell support complex 10 using the thus obtained highly functional cells, it now becomes possible to provide a high performance bioartificial organs and in vitro evaluation system.

This embodiment also includes a step of culturing the renal cells 24 in the state of aggregate 30, with the cell suspension kept stirred. For full restoration of the physiological functions of the renal cells 24, the renal cells 24 are required to be cultured for a predetermined length of time in the state of aggregate 30. Meanwhile, the intermittent stirring step is associated with growth of the aggregate 30. Hence, the intermittent stirring step, if continued for a length of time supposedly enough to restore the physiological functions, would make the aggregate 30 too large. The present inventors have found that the aggregate 30, when grown too large, inhibits restoration of the physiological functions. In contrast in this embodiment, the intermittent stirring step is followed by the continuous stirring step. The continuous stirring step inhibits mutual adhesion of the renal cells 24, and thereby suppresses growth of the aggregate 30. Hence, the physiological functions of the renal cells 24 can be restored more reliably, while avoiding the aggregate 30 from becoming excessively large.

In this embodiment, the rest time in the intermittent stirring step is preset longer than 5 minutes and shorter than 480 minutes. This makes the renal cells 24 mutually adhere more reliably, and can prevent the aggregate 30 from becoming excessively large in a more reliable manner. When stirring the cell suspension in the intermittent stirring step, the rotating speed of the stirring blade 27 of the culture vessel 26 is preset to faster than 20 rpm. This reliably suspends the precipitated renal cells 24 and the aggregate 30, and more reliably adjust the size of aggregate 30.

The culture period of the renal cells 24 in the method of culturing of this embodiment is 5 days or longer and 14 days or shorter. This can more reliably restore the physiological functions of the renal cells 24, and can obtain the cultured cells 16 with the physiological functions strongly expressed. Most cells, when kept in the aggregated state for a long period, would memorize the state, and would become more likely to aggregate. In contrast, with the culture period preset to 14 days or shorter, the cultured cells 16 are prevented from becoming more non-releasable from the aggregate 30, and from becoming more likely to re-aggregate after isolation.

In the method of culturing of this embodiment, the number of renal cells 24 composing the aggregate 30 is 500 or larger and 5000 or smaller. The size of the aggregate 30 is 100 μm or larger and 350 μm or smaller. This successfully improves the workability of the cell culturing, and enables manufacture of the cultured cells 16 that retain good physiological functions in a more reliable manner.

The method of manufacturing the cell support complex 10 of this embodiment includes: coating a coating agent that contains one or more components selected from the group consisting of laminin molecule, basement membrane matrix mixture, collagen molecule and fragment of any of these components, over the base 12; deaggregating the aggregate 30 of the cultured cells 16 formed by the method of culturing of this embodiment into discrete cultured cells 16; and seeding the cultured cell 16 on the base 12, and culturing the cultured cells 16 on the base 12 to thereby form a monolayer structure of the cultured cells 16. With the coating agent layer 14 thus formed by coating, over the base 12, a coating agent that contains a predetermined adhesion molecule, the monolayer structure of the cultured cells 16 can be formed stably over the base 12. This successfully provides the cell support complex 10 with improved stability of the monolayer structure of the cultured cells 16. The base 12 has formed thereon the monolayer composed of the cultured cells 16 that retain high physiological functions. The high functional cell support complex 10 is therefore obtainable.

With the method for manufacturing the cell support complex 10 of this embodiment, the monolayer structure of the cultured cells 16 is stably obtainable. This excludes the need for microscopic observation of confluence of the cultured cells 16 over the base 12. Also artificial membrane is applicable to the base 12. This enables simple manufacture of the cell support complex 10 with a desired shape. It becomes also possible to manufacture a large amount of cell support complexes 10 with the same structure.

Note that the base might alternatively employ any biological scaffold obtained by decellularizing small intestine submucosa from human, sheep, pig and so forth. Such biological scaffold, being derived from living bodies, are however difficult to be manufactured in large quantity with the constant structure. The biological scaffold is therefore not suitable for clinical use such as artificial kidney. Shape of the small intestine submucosa differs one by one, among animal species and among individuals. The area of seeding of cells can therefore vary one by one. The number of cells to be seeded is therefore difficult to control. Intricate shape and opacity of the material also make it difficult to observe the cells. The biological scaffold is therefore not suitable for use in the drug evaluation system in need of cell observation.

Having described in this embodiment a case where the renal cells 24 are cultured by suspension culture, kinds of cells are not limited to the renal cells 24. For example, also pluripotent stem cells such as embryonic stem cell (ES cell) and induced pluripotent stem cell (iPS cell); tissue stem cell differentiated from pluripotent stem cell; progenitor cell; and tissue cell may be cultured by the method of culturing including the intermittent stirring step, to thereby obtain a large amount of cells that retain high pluripotency. The tissue stem cell, progenitor cell and tissue cell may be any of those derived from tissue other than kidney.

The present invention is not limited to the aforementioned embodiments, allowing various modifications and design alterations based on knowledge of those skilled in the art. Also thus modified embodiments fall within the scope of the present invention. Any new embodiments created by combining the aforementioned embodiments with any of modified examples described below will have both effects of the embodiments and modified examples to be combined.

EXAMPLES

Examples of the present invention will be explained below. Examples are merely illustrative ones, and by no means limit the present invention.

Analysis of Gene Expression in Proximal Tubule Epithelial Cell: Test 1

Test 1 was carried out to confirm depression of physiological functions in human proximal tubule epithelial cells. First, 100000 human proximal tubule epithelial cells (from Lonza Inc.) were seeded on a 60 mm diameter petri dish (from Corning Inc.) pre-coated with a gelatin solution (from Sigma Corporation). The cells were cultured using REGM™ (from Lonza Inc.) as a medium under conditions of 37° C. and 5% $CO_2$.

mRNA was extracted from the human proximal tubule epithelial cells immediately after seeding (that is, after 0 hours) and on the 4th day of culture (that is, after 96 hours), using RNEasy® Mini Kit (from QIAGEN), and purified. Next, cDNA was synthesized from each purified mRNA, using QuantiTect® Reverse Transcription Kit (from QIAGEN). Using each cDNA as a template and Thermal Cycler Dice Real Time System I (from Takara Bio Inc.), expression levels of AQP1, CD13, SGLT2, Na/K ATPase, PEPT1, MDR1, OAT1, OCTN2, E-cadherin and ZO-1 genes were measured by real-time PCR.

These genes are related to physiological functions of renal cell. More specifically, AQP1 (aquaporin 1) is a gene coding for a protein involved in water transport. CD13 (alanyl aminopeptidase) is a gene coding for a protein involved in peptidization of protein. SGLT2 (sodium glucose cotransporter 2) is a gene coding for a protein involved in sodium and glucose transport. Na/K ATPase is a gene coding for a protein involved in ion transport. PEPT1 (peptide transporter 1) is a gene coding for a protein involved in peptide transport. MDR1 (multiple drug resistance 1), OAT1 (organic anion transporter 1) and OCTN2 (organic cation transporter novel 1) are genes coding for proteins involved in drug transport. E-cadherin and ZO-1 (zonula occludens-1) are genes coding for proteins involved in intercellular junction.

Ratio of the expression level on the 4th day of culture relative to the expression level immediately after seeding (day4/day0) was determined for each gene. Results are summarized in FIG. 6. FIG. 6 is a chart summarizing time-dependent changes in gene expression levels in the cells after the adhesion culture. As summarized in FIG. 6, the ratio was found to be smaller than one, for all genes. That is, the expression levels of the individual genes on the 4th day of culture were found to decline from the levels immediately after start of culture. The results taught that the human proximal tubule epithelial cells showed declined gene expression levels after two-dimensional culture in the petri dish, that is, dedifferentiation. Note that, even immediately after seeding, the human proximal tubule epithelial cells are supposed to have the physiological functions declined to a certain degree.

Measurement of Gene Expression Levels in Cells Composing Aggregate: Test 2

Test 2 was carried out to confirm restoration of physiological functions of the human proximal tubule epithelial cells in suspension culture. First, a series of suspensions of human proximal tubule epithelial cells (from Lonza Inc.) were prepared with varied cell concentration. The concentration of the individual cell suspension was varied among 5000, 10000, 25000, 50000, 100000 and 250000 cells/ml. On 96 well U-bottom plates with cell-repellent treatment (from Sumitomo Bakelite Co., Ltd.), 100 μl each of the individual cell suspensions was dropped to seed the cells. As a consequence, the number of cells on the individual plates now amounted to 500 cells/well, 1000 cells/well, 2500 cells/well, 5000 cells/well, 10000 cells/well and 25000 cells/well. The cells were cultured using REGM™ (from Lonza Inc.) as a medium under conditions of 37° C. and 5% $CO_2$ (suspension culture). The medium was exchanged every two days.

Meanwhile, on a 96 well flat bottom plate (from Corning Inc.) coated with a gelatin solution (from Sigma Corporation), 100 μl of a cell suspension with the cell concentration adjusted to 10000 cells/ml was dropped to seed the cells. The number of cells now amounts to 1000 cells/well. The cells were cultured using REGM™ (from Lonza Inc.) as a medium under conditions of 37° C. and 5% $CO_2$ (adhesion culture). The medium was exchanged every two days. The preparation was used as Comparative Example (control).

The cells on the individual plates were observed under an optical microscope. The human proximal tubule epithelial cells were confirmed to form the aggregate in the suspension culture. On the other hand, no aggregate was formed in the adhesion culture.

The individual plates with the aggregates formed thereon were subjected to measurement of the diameter of aggregate on the 7th day after seeding. The diameter of aggregate was measured using a measurement software attached to Digital Microscope VHX-500 (from KEYENCE Corporation). The diameter, or the maximum width, of ten aggregates was measured on each of the plates with different number of cells, to find the maximum value and minimum value. From the results, an approximate diameter of the aggregate was found to be 100 to 180 μm for the number of cells of 500 cells/well (that is, an aggregate composed of 500 cells). For the number of cells of 1000 cells/well (that is, an aggregate composed of 1000 cells), an approximate diameter of the aggregate was found to be 150 to 220 μm. For the number of cells of 2500 cells/well (that is, an aggregate composed of 2500 cells), it was found to be 220 to 300 μm. For the number of cells of 5000 cells/well (that is, an aggregate composed of 5000 cells), it was found to be 260 to 350 μm. For the number of cells of 10000 cells/well (that is, an aggregate composed of 10000 cells), it was found to be 370 to 480 μm. For the number of cells of 25000 cells/well (that is, an aggregate composed of 25000 cells), it was found to be 460 to 610 μm.

The individual plates with the aggregates formed thereon were also subjected to measurement of the number of cells composing the aggregates formed on the 3rd, 7th and 14th days after the seeding (that is, 72 hours, 168 hours and 336 hours after). More specifically, the aggregate was individualized with a 0.1% trypsin solution, and 20 aggregates were subjected to measurement using TC20 full-automatic cell counter (from Bio-Rad Laboratories, Inc.) to find the number of cells, and an average value was determined to be the number of constitutive cells of the aggregate. From the results, the number of constitutive cells of the aggregate was found to remain almost unchanged over 14 days. Also the diameter of aggregate was found to remain almost unchanged over 14 days.

For each plate, mRNA was extracted from the human proximal tubule epithelial cells immediately after seeding (that is, after 0 hours) and from the human proximal tubule epithelial cells that compose the aggregate on the 3rd and 7th days of culture (that is, after 72 hours and 168 hours), using RNEasy® Mini Kit (from QIAGEN), and purified. Next, cDNA was synthesized from each of the thus purified mRNA, using QuantiTect® Reverse Transcription Kit (from QIAGEN). Using each cDNA as a template and Thermal Cycler Dice Real Time System I (from Takara Bio Inc.), expression levels of AQP1, SGLT2 and OAT1 genes were measured by real-time PCR.

For each gene, the ratio of expression level on the 3rd day of culture relative to the expression level immediately after seeding (day3/day0), and the ratio of expression level on the 7th day of culture relative to the expression level immediately after seeding (day7/day0) were calculated. Results are summarized in FIG. 7. FIG. 7 is a chart summarizing time-dependent changes in gene expression levels in the cells that compose the aggregates.

As summarized in FIG. 7, expression levels of AQP1 gene and SGLT2 gene were found to be larger after the cells were kept under suspension culture with any number of cells and on any number of days, than in Comparative Example in which the cells were kept under adhesion culture. The tendency was found to be particularly distinctive on the 7th day of culture. Expression level of OAT1 gene was found to be larger in Comparative Example on the 3rd day of culture, but was found to be larger in the cells kept under the suspension culture on the 7th day, except for the case with the number of cells of 25000 cells/well. It was thus confirmed that the cells kept under the suspension culture were more likely to restore the physiological functions of the cells, as compared with the cells kept under the adhesion culture.

From the results of the individual genes on the 7th day of culture, the expression levels of AQP1 gene and OAT1 gene were found to distinctively increase, when the number of cells was 500 cells/well or larger and 5000 cells/well or smaller. It was thus confirmed that the physiological functions were further improved, by adjusting the number of cells controlled within the aforementioned range.

Analysis of Time-Dependent Change of Gene Expression Level in Cell Composing Aggregate: Test 3

Test 3 was carried out to confirm restoration of physiological functions of human proximal tubule epithelial cells in the suspension culture. First, a suspension of human proximal tubule epithelial cells (from Lonza Inc.) was prepared, with the cell concentration adjusted to 10000 cells/ml. On 96 well U-bottom plates with cell-repellent treatment (from Sumitomo Bakelite Co., Ltd.), 100 µl of the cell suspension was dropped to seed the cells (consequently, the number of cells amounts to 1000 cell/well). The cells were cultured using REGM™ (from Lonza Inc.) as a medium under conditions of 37° C. and 5% $CO_2$ (suspension culture) The medium was exchanged every two days.

mRNA was extracted from the human proximal tubule epithelial cells immediately after seeding (that is, after 0 hours) and from the human proximal tubule epithelial cells that compose the aggregate on the 3, 4, 5, 6, 7, 8, 10, 12 and 14th days of culture (that is, 72, 96, 120, 144, 168, 192, 240, 288 and 336 hours after), using RNEasy® Mini Kit (from QIAGEN), and purified. Next, cDNA was synthesized from each of the thus purified mRNA, using QuantiTect® Reverse Transcription Kit (from QIAGEN). Using each cDNA as a template and Thermal Cycler Dice Real Time System I (from Takara Bio Inc.), expression levels of AQP1, SGLT2 and OAT1 genes were measured by real-time PCR.

Ratio of the expression level on the Mth (M=3, 4, 5, 6, 7, 8, 10, 12, 14) day of culture relative to the expression level immediately after seeding (dayM/day0) was determined for each gene. Results are summarized in FIG. 8. FIG. 8 is a chart summarizing time-dependent changes in gene expression levels in the cells that compose the aggregates.

As summarized in FIG. 8, expression levels of AQP1 gene and OAT1 gene were found to sharply increase on the 5th day of culture. High expression level on the 5th day was also found for SGLT2 gene. It was thus confirmed that the cells with further improved physiological functions were obtainable, by presetting the culture period of human proximal tubule epithelial cells to five days or longer. In addition, the expression levels of AQP1 gene and OAT1 gene turned to decline on the 10th day of culture and thereafter. It was thus confirmed that the culture period of human proximal tubule epithelial cells is preferably 10 days or shorter. Note that the expression levels of AQP1 gene and OAT1 gene were kept still higher than the level immediately after seeding, even on the 12 and 14th days. It was thus confirmed that the culture period of human proximal tubule epithelial cells is preferably 14 days or shorter, and more preferably 10 days or shorter.

Culture of Human Proximal Tubule Epithelial Cell Solely by Continuous Stirred Culture: Test 4

Test 4 was carried out to confirm presence or absence of formation of aggregate solely after continuous stirred culture, and gene expression levels in the obtained cells. First, a cell suspension of human proximal tubule epithelial cells (from Lonza Inc.) was prepared, with the cell concentration adjusted to 100000 cells/ml. REGM™ (Lonza Inc.) was used as a medium of the suspension. Eighty milliliter of the suspension was placed in a 100 ml spinner flask (from INTEGRA Biosciences AG). Upon seeding, continuous stirred culture was carried out, while rotating the stirring blade at predetermined levels of rotating speed, under conditions of 37° C. and 5% $CO_2$. The rotating speed of the stirring blade was varied among to 30, 40, 60 and 75 rpm. The medium was exchanged every three days.

On 96 well U-bottom plates with cell-repellent treatment (from Sumitomo Bakelite Co., Ltd.), 200 µl of the suspension of human proximal tubule epithelial cells (from Lonza Inc.) with a cell concentration of 10000 cells/ml was added, and allowed to stand still for seven days (static suspension culture). The preparation was used as the control.

Figures 9A, 9B, 9C:
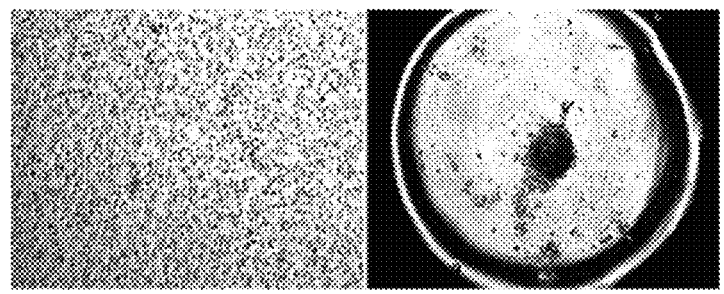
FIG. 9A is a chart summarizing presence or absence of aggregates in continuous stirred culture and static suspension culture.
FIG. 9B shows optical microphotographs of cells obtained after continuous stirred culture and static suspension culture.
FIG. 9C is a chart summarizing time-dependent changes in gene expression levels in cells obtained after continuous stirred culture.

On the 3rd and 7th days, the cell suspension in the spinner flask was transferred onto a 24 well flat bottom plate with cell-repellent treatment (from Sumitomo Bakelite Co., Ltd.). Cell morphology was then observed under a microscope. For the control, the cell morphology was observed as it is under the microscope, without transferring it onto other plate. The content having the aggregate formed therein was evaluated as "o", and the content having no aggregation formed therein was evaluated as "x". Results are summarized in FIG. 9A. FIG. 9B shows microphotographs of representative examples including a cell cultured in the spinner flask at a rotating speed of 60 rpm for 7 days, and a control cell.

FIG. 9A is a chart summarizing presence or absence of aggregates in the continuous stirred culture and the static suspension culture. FIG. 9B shows optical microphotographs of cells obtained after continuous stirred culture and static suspension culture. As summarized and shown in FIGS. 9A and 9B, human proximal tubule epithelial cells were confirmed to form the aggregate in the static suspension culture. Meanwhile, it was confirmed that the aggregate was not formed under the continuous stirred culture at any stirring speed. The cells under the continuous stirred culture were found to suspend in the form of discrete cells.

mRNA was extracted from the cells on the 3rd and 7th days of continuous stirred culture and from the control cell, using RNEasy® Mini Kit (from QIAGEN), and then purified. Next, cDNA was synthesized from each of the thus purified mRNA, using QuantiTect® Reverse Transcription Kit (from QIAGEN). Using each cDNA as a template and Thermal Cycler Dice Real Time System I (from Takara Bio Inc.), expression levels of AQP1 and OAT1 genes were measured by real-time PCR. For each gene, the ratio of expression level on the 3rd day of culture relative to the expression level of the control, and the ratio of expression level on the 7th day of culture relative to the expression level of the control were calculated. Results are summarized in FIG. 9C.

FIG. 9C is a chart summarizing time-dependent changes in gene expression levels in cells obtained after continuous stirred culture. As summarized in FIG. 9C, the expression levels of the individual genes under the continuous stirred culture were confirmed to be low at any stirring speed, as compared with the cells under the static suspension culture.

Analysis of Gene Expression Level in Cell Obtained by Continuous Stirred Culture of Aggregate: Test 5

Test 5 was carried out to confirm influence of the stirred culture on the cells composing the aggregate. First, a suspension of human proximal tubule epithelial cells (from Lonza Inc.) was prepared, with the cell concentration adjusted to 10000 cells/ml. REGM™ (Lonza Inc.) was used as a medium of the suspension. On a 96 well U-bottom plate with cell-repellent treatment (from Sumitomo Bakelite Co., Ltd.), 200 µl of the cell suspension was dropped to seed the cells. The cells were then cultured by the static suspension culture under conditions of 37° C. and 5% $CO_2$ for 3 days.

The obtained aggregate was transferred into a 100 ml spinner flask (from INTEGRA Biosciences AG). The aggregate was then kept under the continuous stirred culture under conditions of 37° C. and 5% $CO_2$ for 4 days, while rotating the stirring blade at a predetermined rotating speed. The culture period became seven days in total. The rotating speed of the stirring blade was varied among to 30, 40, 60 and 75 rpm.

mRNA was extracted from the cells on the 4th day of the continuous stirred culture, using RNEasy® Mini Kit (from QIAGEN), and then purified. Next, cDNA was synthesized from each of the thus purified mRNA, using QuantiTect® Reverse Transcription Kit (from QIAGEN). Using each cDNA as a template and Thermal Cycler Dice Real Time System I (from Takara Bio Inc.), expression levels of AQP1 and OAT1 genes were measured by real-time PCR. For each gene, the ratio of expression level relative to the expression level of the control used in Test 4 (seven-day static suspension culture) was calculated. Results are summarized in FIG. 10.

FIG. 10 is a chart summarizing gene expression levels of the cells obtained after continuous stirred culture of the aggregates. As summarized in FIG. 10, when the aggregate was formed in the static suspension culture, followed by the continuous stirred culture, the cells were confirmed to express the genes up to levels equivalent to those of the cells not subjected to the continuous stirred culture. That is, stirring per se of the cell suspension was confirmed to be not influential to gene expression of the cells. This enabled the present inventors to predict establishment of a culture system in which cells are proliferated in a petri dish or the like, then transferred into a spinner flask while being kept in the form of discrete cells, and kept under the stirred suspension culture while forming the aggregate in the flask. Such culture system can produce, at a time, a large amount of cultured cells that retain gene activities equivalent to those in the cells resulted from the static suspension culture.

Intermittent Stirred Culture of Cells Under Various Conditions: Test 6

Test 6 was carried out to confirm geometry of the cells resulted after the intermittent stirred culture under various conditions, and to determine culture conditions suitable for forming the aggregate. First, a cell suspension of human proximal tubule epithelial cells (from Lonza Inc.) was prepared, with the cell concentration adjusted to 100000 cells/ml. REGM™ (Lonza Inc.) was used as a medium of the suspension. Eighty milliliter of the cell suspension was placed in a 100 ml spinner flask (from INTEGRA Biosciences AG). The content was then allowed to stand still for 10 minutes.

Next, as a first experimental system, the intermittent stirred culture repeating the cycles of 10-minute stirring and predetermined-minute rest (standstill) was carried out for 10 hours. The rest time was varied among 0, 5, 10, 30, 60, 120, 240 and 480 minutes. The 0-minute rest means the continuous stirred culture. The rotating speed (stirring speed) of the stirring blade during stirring was preset to 40 rpm.

Meanwhile, as a second experimental system, the intermittent stirred culture repeating the cycles of 10-minute stirring and 10-minute rest was carried out for 10 hours. The rotating speed of the stirring blade was varied among 20, 30, 40, 60 and 75 rpm.

Figure 11:
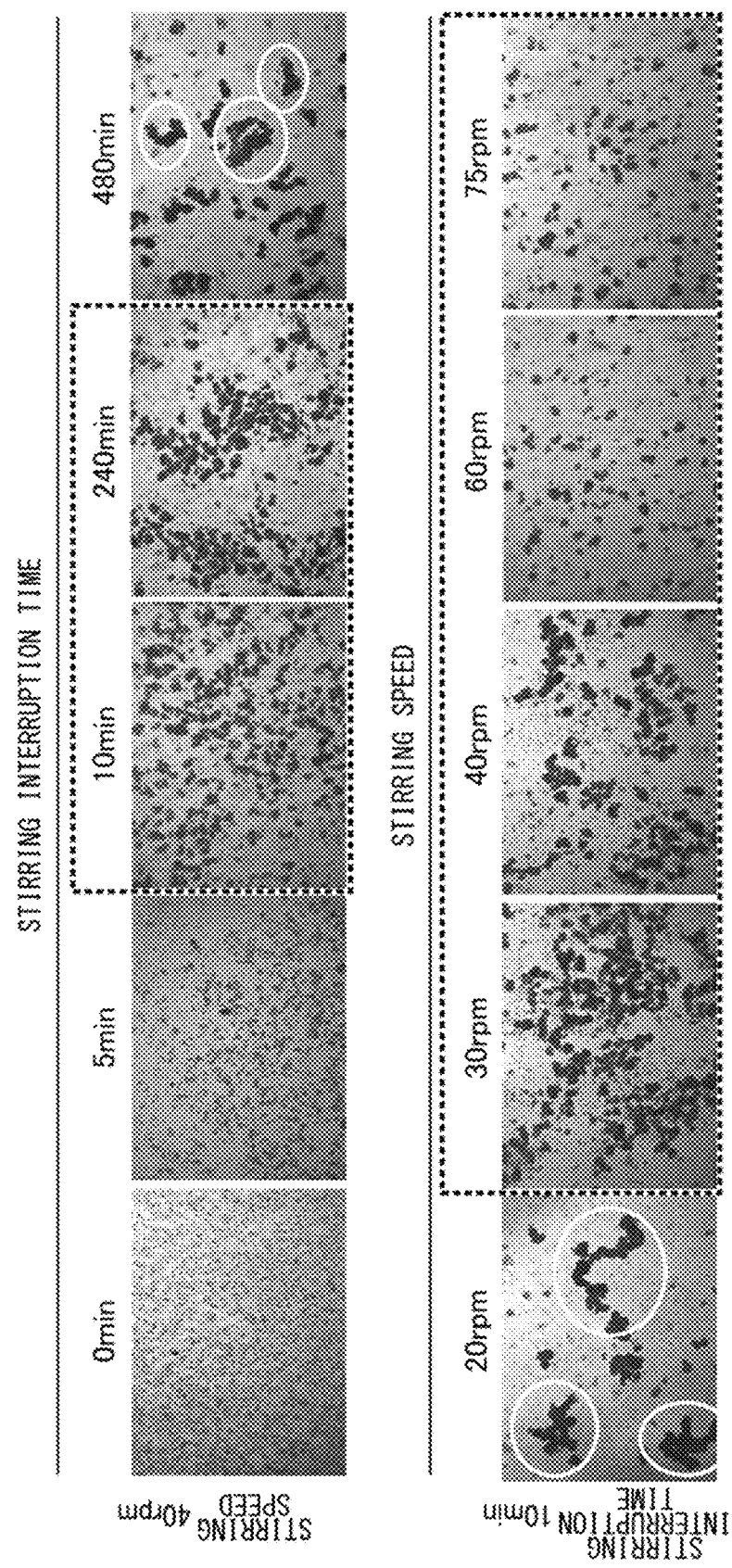
FIG. 11 shows optical microphotographs of cells obtained under various conditions of intermittent stirred culture.

In both of the first and second experimental systems, the intermittent stirred culture was followed by the continuous stirred culture under conditions of 37° C. and 5% $CO_2$ for 7 days. The rotating speed of the stirring blade in the continuous stirred culture was preset to the same speed as in the intermittent stirred culture. The medium was exchanged every two days. Upon completion of the continuous stirred culture, the cell suspension in the spinner flask was transferred onto a 24 well flat bottom plate with cell-repellent treatment (from Sumitomo Bakelite Co., Ltd.). Cell morphology was then observed under a microscope. Results are shown in FIG. 11. FIG. 11 shows optical microphotographs of the cells obtained under various conditions of the intermittent stirred culture.

The content having formed therein a uniform size of aggregates was evaluated as "o", the content having formed therein non-uniform size of aggregates was evaluated as "Δ", and the content having formed therein no aggregate was evaluated as "x". Note that the non-uniform size of aggregates include excessively large aggregate formed by mutual adhesion of aggregates, and excessively small aggregate resulted from insufficient adhesion among the cells. Results are summarized in FIG. 12. FIG. 12 is a chart summarizing presence or absence of aggregate in the intermittent stirred culture under various conditions.

As shown in FIG. 11 and FIG. 12, the aggregate was not formed for the case where the rest time in the intermittent stirred culture was 0 minutes, that is, for the case where the continuous stirred culture was solely carried out, at stirring speeds of 30, 40, 60 and 75 rpm. It was thus confirmed that the intermittent stirred culture is necessary to obtain a plurality of aggregates with uniform size.

With the stirring speed preset to 20 rpm, the aggregate was formed even solely by the continuous stirred culture (with the rest time of 0 minutes), although accompanied by non-uniformity. With the stirring speed preset to 20 rpm, non-uniform and excessively large aggregates were formed by the intermittent stirred culture at any rest time. In FIG. 11, a microphotograph indicated by a stirring interruption time of 10 minutes and a stirring speed of 20 rpm shows lumps circled by bright lines, which are aggregates with non-uniform sizes. It was thus confirmed that the stirring speed of 20 rpm was insufficient for the purpose of controlling the size of aggregate, while suspending the cells and aggregates. That is, the stirring speed of 20 rpm was as good as the state of static culture, supposedly failed in suppressing mutual adhesion of the aggregates, and resulted in formation of non-uniform and excessively large aggregates.

On the other hand, even with the stirring speed faster than 20 rpm, non-uniform and excessively small aggregates were formed, when the rest time was preset to five minutes. It was thus confirmed that the rest time of five minutes was insufficient for the cells to mutually adhere in a reliable manner. Even with the stirring speed faster than 20 rpm, non-uniform and excessively large aggregates were formed, when the rest time was preset to 480 minutes. In FIG. 11, a microphotograph indicated by a stirring speed of 40 rpm and a stirring interruption time of 480 minutes shows lumps circled by bright lines, which are aggregates with non-uniform sizes. It was thus confirmed that the rest time of 480 minutes was too long for the aggregates to avoid mutual adhesion in a reliable manner.

It was also confirmed that the faster the stirring speed, the longer the rest time during which the aggregates with a uniform size can be formed. More specifically, under the stirring speed of 30 rpm, the aggregates with a uniform size were formed at the rest times of 10 minutes and 30 minutes. Under stirring speeds of 40, 60 and 75 rpm, the aggregates with a uniform size were formed at the rest time individually ranging from 10 minutes to 240 minutes.

Cells precipitate during the rest time, and adhere to the other cells. The aggregates are thus formed. Hence, the longer the rest time, the longer the growth time of aggregate. Results of this test indicate that, with the stirring speed preset to faster than 20 rpm, and even 30 rpm, the aggregates formable at the rest time shorter than 60 minutes will be suspended more reliably. That is, with the stirring speed preset to faster than 20 rpm, and even 30 rpm, the aggregates formable at the rest time shorter than 60 minutes will be prevented from adhering with each other, and can keep a uniform size. Moreover, with the stirring speed preset to 40 rpm or faster, the aggregates formable at the rest time shorter than 480 minutes will be suspended in a more reliable manner, and will be prevented from adhering with each other.

Analysis of Gene Expression Levels in Cells Obtained by Intermittent Stirred Culture at Varied Rest Time: Test 7

Test 7 was carried out to confirm changes in the gene expression levels in the cells under the intermittent stirred culture at varied rest time. First, a cell suspension of human proximal tubule epithelial cells (from Lonza Inc.) was prepared, with the cell concentration adjusted to 100000 cells/ml. REGM™ (Lonza Inc.) was used as a medium of the suspension. Eighty milliliter of the suspension was placed in a 100 ml spinner flask (from INTEGRA Biosciences AG). The content was then allowed to stand still for 10 minutes.

Next, the intermittent stirred culture repeating the cycles of 10-minute stirring and predetermined-minute rest was carried out for 10 hours. The rest time (stirring interruption time) was varied among 0, 5, 10, 60 and 240 minutes. The 0-minute rest means the continuous stirred culture. The rotating speed (stirring speed) of the stirring blade during stirring was preset to 40 rpm. The intermittent stirred culture was followed by the continuous stirred culture under conditions of 37° C. and 5% $CO_2$ for 7 days. The rotating speed of the stirring blade in the continuous stirred culture was preset to the same speed as in the intermittent stirred culture. The medium was exchanged every two days. As also shown in Test 6, with the stirring speed preset to 40 rpm, the aggregates with a uniform size were not formed at the rest times of 0 and 5 minutes, meanwhile the aggregates with a uniform size were formed at the rest times of 10, 60 and 240 minutes.

Upon completion of the continuous stirred culture, mRNA was extracted from the cells using RNEasy® Mini Kit (from QIAGEN), and then purified. Next, cDNA was synthesized from each of the thus purified mRNA, using QuantiTect® Reverse Transcription Kit (from QIAGEN). Using each cDNA as a template and Thermal Cycler Dice Real Time System I (from Takara Bio Inc.), expression levels of AQP1 and OAT1 genes were measured by real-time PCR. For each gene, the ratio of expression level relative to the expression level of the control used in Test 4 (seven-day static suspension culture) was calculated. Results are summarized in FIG. 13.

FIG. 13 is a chart summarizing gene expression levels in cells after the intermittent stirred culture with varied rest time. As summarized in FIG. 13, the cells obtained after the intermittent stirred culture at the rest times of 0 and 5 minutes were confirmed to show the expression levels of the individual genes lower than those of the control. In contrast, at the rest times of 10, 60 and 240 minutes, the expression levels of the individual genes were confirmed to be equivalent to those of the control. This is supposedly because the formation of aggregates was insufficient at the rest times of 0 and 5 minutes, meanwhile the aggregates with a uniform size were formed at the rest times of 10, 60 and 240 minutes.

Analysis of Gene Expression Levels in Cells Obtained by Intermittent Stirred Culture at Varied Stirring Speed: Test 8

Test 8 was carried out to confirm changes in the gene expression levels in the cells obtained after the intermittent stirred culture at varied rest time. First, a cell suspension of human proximal tubule epithelial cells (from Lonza Inc.) was prepared, with the cell concentration adjusted to 100000 cells/ml. REGM™ (Lonza Inc.) was used as a medium of the suspension. Eighty milliliter of the cell suspension was placed in a 100 ml spinner flask (from INTEGRA Biosciences AG). The content was then allowed to stand still for 10 minutes.

Next, the intermittent stirred culture repeating the cycles of 10-minute stirring and 10-minute rest was carried out for 10 hours. The rotating speed (stirring speed) of the stirring blade was varied among 30, 40, 60 and 75 rpm. The intermittent stirred culture was followed by the continuous stirred culture under conditions of 37° C. and 5% $CO_2$ for 7 days. The rotating speed of the stirring blade in the continuous stirred culture was preset to the same speed as in the intermittent stirred culture. The medium was exchanged every two days. As also taught by Test 6, the aggregates with a uniform size were formed at the rest time of 10 minutes, at all stirring speeds of 30, 40, 60 and 75 rpm.

Upon completion of the continuous stirred culture, mRNA was extracted from the cells using RNEasy® Mini Kit (from QIAGEN), and then purified. Next, cDNA was synthesized from each of the thus purified mRNA, using QuantiTect® Reverse Transcription Kit (from QIAGEN). Using each cDNA as a template and Thermal Cycler Dice Real Time System I (from Takara Bio Inc.), expression levels of AQP1 and OAT1 genes were measured by real-time PCR. For each gene, the ratio of expression level relative to the expression level of the control used in Test 4 (seven-day static suspension culture) was calculated. Results are summarized in FIG. 14.

FIG. 14 is a chart summarizing gene expression levels of the cells obtained after the stirred culture with varied stirring speed. As summarized in FIG. 14, the cells obtained after the intermittent stirred culture at any stirring speed were confirmed to show the expression levels of the individual genes equivalent to those of the control. It was thus confirmed that the stirring speed is less influential on the gene expression levels, if only the cell aggregate were formed. It was also confirmed that the slower the stirring speed, the larger the aggregate.

Intermittent Stirred Culture of Human iPS Cells at Varied Rest Time: Test 9

Test 9 was carried out to confirm the geometry of human iPS cells obtained after the intermittent stirred culture. First, a suspension of human iPS cells was prepared, with the cell concentration adjusted to 100000 cells/ml. For a medium of the suspension, StemFit® (from Ajinomoto Co., Inc.) containing 10 μM of Y-27632 (from Cosmo Bio Co., Ltd.) added thereto was used. Y-27632 is a ROCK (Rho-associated coiled-coil forming kinase) inhibitor, and particularly suppresses cell death of human iPS cells. Fifty milliliter of the cell suspension was placed in each of a plurality of 100 ml spinner flasks (from INTEGRA Biosciences AG). The initial number of cells in each flask therefore amounts to 5×10$^6$.

A part of the spinner flasks were then allowed to stand still for 10 minutes, followed by the intermittent stirred culture for 1.5 hours, while repeating the cycles of one-minute stirring and 10-minute rest. The residual spinner flasks were allowed to stand still for 15 minutes, followed by the intermittent stirred culture for 1.5 hours, while repeating the cycles of one-minute stirring and 15-minute rest. The rotating speed (stirring speed) of the stirring blade during stirring was preset to 40 rpm for all flasks. The medium was exchanged every day.

For all spinner flasks, the intermittent stirred culture was followed by the continuous stirred culture under conditions of 37° C. and 5% $CO_2$ for 5 days. The rotating speed of the stirring blade in the continuous stirred culture was preset to the same speed as in the intermittent stirred culture. The medium was exchanged every two days. Upon completion of the continuous stirred culture, the cell suspension in the spinner flask was transferred onto a 24 well flat bottom plate with cell-repellent treatment (from Sumitomo Bakelite Co., Ltd.). Cell morphology was then observed under a microscope.

Figure 15B:
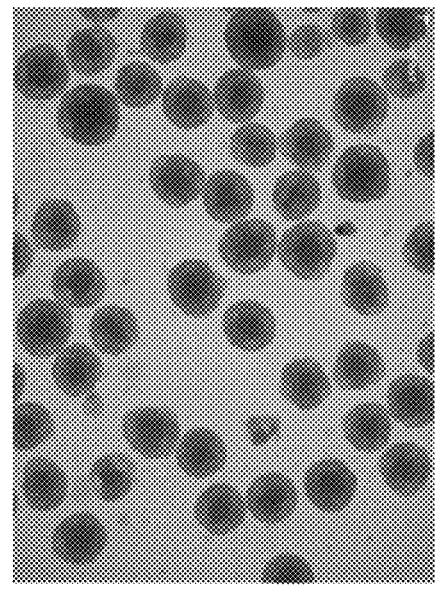
FIG. 15A and FIG. 15B are optical microphotographs of human iPS cells obtained after intermittent stirred culture with varied rest time.
Figure 15A:
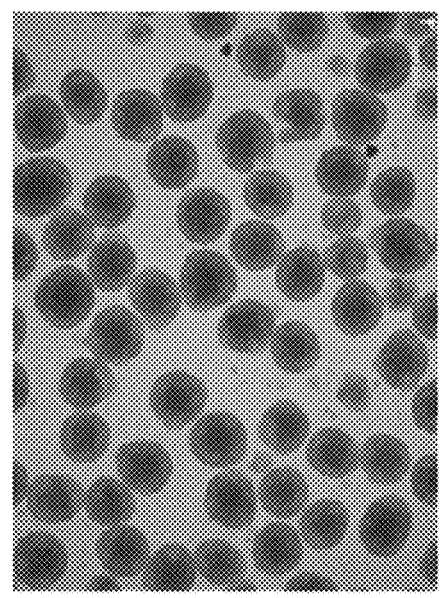

Results are shown in FIG. 15A and FIG. 15B. FIG. 15A and FIG. 15B are optical microphotographs of human iPS cells obtained after the intermittent stirred culture with varied rest time. FIG. 15A shows a result at the rest time of 10 minutes, and FIG. 15B shows a result at the rest time of 15 minutes. In FIG. 15A and FIG. 15B, each of a plurality of black circular lumps represents an aggregate of human iPS cells. This test therefore confirmed that the aggregates of human iPS cells can be formed by carrying out the intermittent stirred culture.

After completion of the continuous stirred culture, the whole amount of the aggregates in each spinner flask was collected, and was individualized into discrete cells by digestion using Accutase® (from Lonza Inc.) for 12 minutes. The number of cells was then counted using TC20 full-automatic cell counter (from Bio-Rad Laboratories, Inc.). The results taught that the number of cells obtained after the intermittent stirred culture at the rest time of 10 minutes amounted to $2.6 \times 10^7$, and the number of cells obtained after the intermittent stirred culture at the rest time of 15 minutes amounted to $3.3 \times 10^7$. Hence the ratios of increase of cells from the initial number of cells were found to be 5.2 times and 6.6 times for the individual intermittent stirred cultures.

Intermittent Stirred Culture of Human iPS Cells at Y-27632 Concentration Varied from Test 9: Test 10

Y-27632 suppresses cell death of human iPS cells. Y-27632 therefore acts to promote aggregation of human iPS cells. Test 10 was then carried out to confirm whether human iPS cells can form the aggregate in the intermittent stirred culture even under a condition with reduced influence of Y-27632.

First, a suspension of human iPS cells was prepared, with the cell concentration adjusted to 100000 cells/ml. For a medium of the suspension, StemFit® (from Ajinomoto Co., Inc.) containing 2 µM of Y-27632 (from Cosmo Bio Co., Ltd.) added thereto was used. The concentration of Y-27632 is now one-fifth of the concentration in the medium used in Test 9. Fifty milliliter of the cell suspension was placed in a 100 ml spinner flask (from INTEGRA Biosciences AG). The initial number of cells amounts to $5 \times 10^6$. The content was then allowed to stand still for 60 minutes. Next, the intermittent stirred culture repeating the cycles of one-minute stirring and 60-minute rest was carried out for 5 hours. The rotating speed of the stirring blade was preset to 40 rpm. The medium was exchanged every day.

The intermittent stirred culture was followed by the continuous stirred culture under conditions of 37° C. and 5% $CO_2$ for 5 days. The rotating speed of the stirring blade in the continuous stirred culture was preset to the same speed as in the intermittent stirred culture. The medium was exchanged every two days. Upon completion of the continuous stirred culture, the cell suspension in the spinner flask was transferred onto a 24 well flat bottom plate with cell-repellent treatment (from Sumitomo Bakelite Co., Ltd.). Cell morphology was then observed under a microscope. Aggregates of human iPS cells were observed as a consequence. It was therefore confirmed that the intermittent stirred culture can form the aggregates of human iPS cells, even under reduced concentration of Y-27632 in the medium. It is therefore considered that the intermittent stirred culture dominantly affects the aggregation of human iPS cells.

After completion of the continuous stirred culture, the whole amount of the aggregates in each spinner flask was collected, and was individualized into discrete cells by digestion using Accutase® (from Lonza Inc.) for 12 minutes. The number of cells was then counted using TC20 full-automatic cell counter (from Bio-Rad Laboratories, Inc.). The number of cells were then found to be $1.8 \times 10^7$. Hence the ratio of increase of cells from the initial number of cells, as a result of the intermittent stirred culture, was found to be 3.6 times.

What is claimed is:

1. A method of culturing cells comprising:
    culturing the cells in a cell suspension under repetitive cycles of stirring and rest while keeping the cells non-adherent to a culture vessel, wherein the culture vessel is treated by cell-repellent treatment or composed of a cell-repellent material,
    forming at least one aggregate of the cells without applying a support in the cell suspension; and
    subsequent to the steps of forming at least one aggregate and culturing the cells under repetitive cycles of stirring and rest, culturing the cells in a state of aggregate, with the cell suspension kept stirred.

2. The method of culturing cells according to claim 1, wherein rest time is longer than 5 minutes and shorter than 480 minutes.

3. The method of culturing cells according to claim 1, wherein the culture vessel has a stirring blade for stirring the cell suspension, with a rotating speed exceeding 20 rpm.

4. The method of culturing cells according to claim 1, wherein the stirring applies a shear stress of 0.3 N/m2 or smaller in absolute value to the cells.

5. The method of culturing cells according to claim 1, wherein culture period of the cells is between 5 days and 14 days.

6. The method of culturing cells according to claim 1, wherein the aggregate is composed of cells with numbers between 500 and 5000.

7. The method of culturing cells according to claim 1, wherein size of the aggregate is between 100 µm and 350 µm.

8. The method of culturing cells according to claim 1, wherein the cells are dedifferentiated cells, and restore the physiological functions of the cells by forming the aggregate.

9. The method of culturing cells according to claim 1, wherein the rest time is between 10 minutes and 30 minutes.

10. The method of culturing cells according to claim 1, wherein the cells are renal cells.

11. The method of culturing cells according to claim 1, further comprising seeding the cells in the culture vessel with a medium and resting the cells for a predetermined duration of time,
   wherein the step of culturing the cells in the cell suspension is performed after resting the cells in the medium.

* * * * *